United States Patent
Chauhan et al.

(10) Patent No.: US 11,298,069 B2
(45) Date of Patent: Apr. 12, 2022

(54) METHOD AND SYSTEM FOR ASSESSING QRS COMPONENTS AND THE RISK OF VENTRICULAR ARRHYTHMIAS

(71) Applicant: University Health Network, Toronto (CA)

(72) Inventors: Vijay Singh Chauhan, Toronto (CA); Adrian Michael Suszko, Toronto (CA)

(73) Assignee: University Health Network, Toronto (CA)

( * ) Notice: Subject to any disclaimer, the term of this patent is extended or adjusted under 35 U.S.C. 154(b) by 814 days.

(21) Appl. No.: 15/575,527

(22) PCT Filed: May 19, 2016

(86) PCT No.: PCT/CA2016/050567
§ 371 (c)(1),
(2) Date: Nov. 20, 2017

(87) PCT Pub. No.: WO2016/183683
PCT Pub. Date: Nov. 24, 2016

(65) Prior Publication Data
US 2018/0125385 A1 May 10, 2018

Related U.S. Application Data

(60) Provisional application No. 62/164,046, filed on May 20, 2015.

(51) Int. Cl.
*A61B 5/366* (2021.01)
*A61B 5/00* (2006.01)
(Continued)

(52) U.S. Cl.
CPC ............ *A61B 5/366* (2021.01); *A61B 5/0006* (2013.01); *A61B 5/316* (2021.01); *A61B 5/333* (2021.01);
(Continued)

(58) Field of Classification Search
None
See application file for complete search history.

(56) References Cited

U.S. PATENT DOCUMENTS 4,073,011 A * 2/1978 Cherry .................. A61B 5/337
360/73.01
5,341,811 A * 8/1994 Cano .................... A61B 5/0428
600/508
(Continued)

FOREIGN PATENT DOCUMENTS

CA         2253760 A1    11/1997
WO      2016183683 A1    11/2016

OTHER PUBLICATIONS

Vanderheyden M, Mullens W, Delrue L, Goethals M, de Bruyne B, Wijns W, Geelen P, Verstreken S, Wellens F, Bartunek J. Myocardial gene expression in heart failure patients treated with cardiac resynchronization therapy responders versus nonresponders. J Am Coll Cardiol. 2008; 51:129-136.
(Continued)

*Primary Examiner* — Michael W Kahelin
*Assistant Examiner* — Elizabeth K So
(74) *Attorney, Agent, or Firm* — Bereskin & Parr LLP/S.E.N.C.R.L., s.r.l.; Tony Orsi; T. Cameron Gale

(57) ABSTRACT

Various embodiments are described herein for a system and a method for assessing a risk of ventricular arrhythmias for a patient. For example, the method may comprise receiving ECG data obtained from the patient; analyzing the ECG data to detect abnormal QRS peaks; determining the risk of ventricular arrhythmias for the patient based on the detected abnormal QRS peaks; and providing an indication of the risk of ventricular arrhythmias for the patient. The system may be configured to perform this method.

20 Claims, 17 Drawing Sheets

(51) Int. Cl.

| | |
|---|---|
| *A61B 5/35* | (2021.01) |
| *A61B 5/316* | (2021.01) |
| *A61B 5/333* | (2021.01) |
| *A61B 5/339* | (2021.01) |
| *A61B 5/363* | (2021.01) |

(52) U.S. Cl.
CPC ............... *A61B 5/339* (2021.01); *A61B 5/35* (2021.01); *A61B 5/363* (2021.01); *A61B 5/7282* (2013.01); *A61B 5/7475* (2013.01); *A61B 5/7217* (2013.01); *A61B 5/7275* (2013.01)

(56) References Cited

U.S. PATENT DOCUMENTS

| | | | |
|---|---|---|---|
| 5,609,158 | A | 3/1997 | Chan |
| 5,891,047 | A | 4/1999 | Lander et al. |
| 6,512,945 | B1* | 1/2003 | Hoium .................. A61B 5/0472 600/515 |
| 7,142,907 | B2 | 11/2006 | Xue et al. |
| 8,285,371 | B2 | 10/2012 | Li et al. |
| 8,437,839 | B2 | 5/2013 | Lux |
| 2011/0111525 | A1* | 5/2011 | Struck ................ G01N 33/6893 436/501 |
| 2011/0319954 | A1* | 12/2011 | Niazi ................... A61N 1/3627 607/17 |
| 2012/0197148 | A1 | 8/2012 | Levitan et al. |

OTHER PUBLICATIONS

Wang J, Gong X, Chen H, Qin S, Zhou N, Su Y, Ge J. Effect of Cardiac Resynchronization Therapy on Myocardial Fibrosis and Relevant Cytokines in a Canine Model With Experimental Heart Failure. J Cardiovasc Electrophysiol. 2017; 28:438-445.

Morita H, Kusano KF, Miura D, Nagase S, Nakamura K, Morita ST, Ohe T, Zipes DP, Wu J. Fragmented QRS as a marker of conduction abnormality and a predictor of prognosis of Brugada syndrome. Circulation. 2008; 118: 1697-704.

Bilchick KC, Kuruvilla S, Hamirani YS, Ramachandran R, Clarke SA, Parker KM, Stukenborg GJ, Mason P, Ferguson JD, Moorman JR, Malholtra R, Mangrum JM, Darby AE, Dimarco J, Holmes JW, Salerno M, Kramer CM, Epstein FH. Impact of mechanical activation, scar and electrical timing on cardiac resynchronization therapy response and clinical outcomes. J Am Coll Cardiol. 2014; 63: 1657-1666.

Yancy CW, Jessup M, Bozkurt B, Butler J, Casey DE Jr, Drazner MH, Fonarow GC, Geraci SA, Horwich T, Januzzi JL, Johnson MR, Kasper EK, Levy WC, Masoudi FA, McBride PE, McMurray JJ, Mitchell JE, Peterson PN, Riegel B, Sam F, Stevenson LW, Tang WH, Tsai EJ, Wilkoff BL; ACCF; AHA Task Force on Practice Guidelines. 2013 ACCF/AHA guideline for the management of heart failure: a report of the American College of Cardiology Foundation/American Heart Assoc Task Force on Practice Guidelines. J Am Coll Cardiol. 2013; 62:e147-239.

N. C. Flowers, L. G. Horan, J. R. Thomas, and W. J. Tolleson, "The anatomic basis for high-frequency components in the electrocardiogram," Circulation, vol. 39, No. 4, pp. 531-539, 1969.

H. E. I. K. Riekkinen and P. E. N. T. Rautahaiju, "Body position, electrode level, and respiration effects on the Frank lead electrocardiogram," Circulation, vol. 53, No. 1, pp. 40-45, 1976.

P. Lander, P. Gomis, R. Goyal, E. J. Berbari, P. Caminal, R. Lazzara, and J. S. Steinberg, "Analysis of abnormal intra-QRS potentials Improved predictive value for arrhythmic events with the signal-averaged electrocardiogram," Circulation, vol. 95, No. 6, pp. 1386-1393, 1997.

C. C. Lin, "Enhancement of accuracy and reproducibility of parametric modeling for estimating abnormal intra-QRS potentials in signal-averaged electrocardiograms," Medical engineering & physics, vol. 30, No. 7, pp. 834-842, 2008.

P. Korhonen, T. Husa, T. Konttila, I. Tierala, M. Makijarvi, H. Vaananen, J. Ojanen, A. Vehtari, and L. Toivonen, "Fragmented QRS in prediction of cardiac deaths and heart failure hospitalizations after myocardial infarction," Annals of Noninvasive Electrocardiology, vol. 15, No. 2, pp. 130-137, 2010.

J. Pan and W. J. Tompkins, "A real-time QRS detection algorithm," Biomedical Engineering, IEEE Transactions on, No. 3, pp. 230-236, 1985.

S. E. Bobbs, N. M. Schmitt, and H. S. Ozemek, "QRS detection by template matching using real-time correlation on a microcomputer," Journal of clinical engineering, vol. 9, No. 3, pp. 197-212, 1984.

C. R. Meyer and H. N. Keiser, "Electrocardiogram baseline noise estimation and removal using cubic splines and state-space computation techniques," Computers and Biomedical Research, vol. 10, No. 5, pp. 459-470, 1977.

G. Breithardt, M. E. Cain, N. El-Sherif, N. C. Flowers, V. Hombach, M. Janse, M. B. Simson, and G. Steinbeck, "Standards for analysis of ventricular late potentials using high-resolution or signal-averaged electrocardiography: a statement by a task force committee of the European Society of Cardiology, the American Heart Association, and the American College of Cardiology," Journal of the American College of Cardiology, vol. 17, No. 5, pp. 999-1006, 1991.

International Search Report and Written Opinion, PCT application No. PCT/CA2016/050567, dated Jul. 6, 2016.

Gomis et al., "Analysis of abnormal signals within the QRS complex of the high-resolution electrocardiogram" Biomedical Engineering, IEEE Transactions on, vol. 44, No. 8, pp. 681-693, Aug. 1997.

Suszko et al., "Quantifying abnormal QRS peaks using a novel time-domain peak detection algorithm: Application in patients with cardiomyopathy at risk of sudden death", 2015 IEEE International Conference on Electro/Information Technology (EIT), pp. 20-24, May 23, 2015.

Endt et al., "Fragmentation of bandpass-filtered QRS-complex of patients prone to malignant arrhythmia," Medical and Biological Engineering and Computing, vol. 36, No. 6, pp. 723-728, Nov. 1998.

Lee DS, Hardy J, Yee R, Healey JS, Birnie D, Simpson CS, Crystal E, Mangat I, Nanthakumar K, Wang X, Krahn AD, Dorian P, Austin PC, Tu JV; Investigators of the Ontario ICD Database. Clinical Risk Stratification for Primary Prevention Implantable Cardioverter Defibrillators. Circ Heart Fail. Sep. 2015;8(5):927-37.

Das MK, Saha C, El Masry H, et al. Fragmented QRS on a 12-lead ECG: A predictor of mortality and cardiac events in patients with coronary artery disease. Heart Rhythm 2007;4:1385-1392.

Breslow, N. E., "Analysis of Survival Data under the Proportional Hazards Model", International Statistical Review / Revue Internationale de Statistique, 43(1): pp. 45-57, 1975.

Zheng et al. "Sudden Cardiac Death in the United States, 1989 to 1998", Circulation, 2001; 104; 2158-2163.

Bayes de Luna A et al., "Ambulatory sudden cardiac death: Mechanisms of production of fatal arrhythmia on the basis of date from 157 cases", Am Heart Journal, Jan. 1989; vol. 117, No. 1, pp. 151-159.

Hauser et al., "Lessons From the Failure and Recall of an Implantable Cardioverter-Defibrillator", Circ 2005; 112: 2040-2042.

Kuchar et al., Prediction of Serious Arrhythmic Events After Myocardial Infarction: Signal-Averaged Electrocardiogram, Holter Monitoring and Radionuclide Ventriculography, JACC 1987, vol. 9, No. 3, pp. 531-538.

Rosengarten et al., "Can QRS scoring predict left ventricular scar and clinical outcomes?", Europace 2013; 15: 1034-41.

Brenyo et al., "QRS Fragmentation and the Risk of Sudden Cardiac Death in MADIT II", J. Cardiovasc Electrophysiol 2012, vol. 23, No. 12, pp. 1343-1348.

M.E.Cain et al., "Signal-averaged electrocardiography," Journal of the American College of Cardiology, vol. 27, No. 1, pp. 238-249, 1996.

Auricchio A, Fantoni C, Regoli F, Carbucicchio C, Goette A, Geller C, Kloss M, Klein H. Characterization of left ventricular activation in patients with heart failure and left bundle-branch block. Circulation. 2004; 109:1133-1139.

(56) References Cited

OTHER PUBLICATIONS

Auricchio A, Lumens J, Prinzen FW. Does Cardiac Resynchronization Therapy Benefit Patients With Right Bundle Branch Block: Cardiac Resynchronization Therapy Has a Role in Patients With Right Bundle Branch Block. Circ Arrhythm Electrophysiol. 2014; 7:532-542.

Birnie DH, Ha A, Higginson L, Sidhu K, Green M, Philippon F, Thibault B, Wells G, Tang A. Impact of QRS morphology and duration on outcomes after cardiac resynchronization therapy: Results from the Resynchronization-Defibrillation for Ambulatory Heart Failure Trial (RAFT). Circulation Heart Fail. 2013; 6:1190-1198.

Bleeker GB, Bax JJ, Fung JW, van der Wall EE, Zhang Q, Schalij MJ, Chan JY, Yu CM. Clinical versus echocardiographic parameters to assess response to cardiac resynchronization therapy. Am J Cardiol. 2006; 97:260-3.

Celikyurt U, Agacdiken A, Sahin T, Al N, Vural A, Ural D. Relationship between fragmented QRS and response to cardiac resynchronization therapy. J Interv Card Electrophysiol. 2012; 35:337-42.

Celikyurt U, Karauzum K, Sahin T, Agacdiken A, Vural A, Ural D. Association between resolution of fragmented QRS and response to cardiac resynchronization therapy. Ann Noninvasive Electrocardiol. 2015; 20:126-31.

Cintron G, Johnson G, Francis G, Cobb F, Cohn JN. Prognostic significance of serial changes in left ventricular ejection fraction in patients with congestive heart failure. The V-HeFT VA Cooperative Studies Group. Circulation. 1993; 87:VI17-23 (abstract only).

Das MK, Suradi H, Maskoun W, Michael MA, Shen C, Peng J, Dandamudi G, Mahenthiran J. Fragmented wide QRS on a 12-lead ECG: a sign of myocardial scar and poor prognosis. Circ Arrhythm Electrophysiol. 2008; 1:258-268.

Das MK, Zipes DP: Fragmented QRS: a predictor of mortality and sudden cardiac death. Heart Rhythm. 2009; 6:S8-14.

Das MK, Maskoun W, Shen C, Michael MA, Suradi H, Desai M, Subbarao R, Bhakta D. Fragmented QRS on twelve-lead electrocardiogram predicts arrhythmic events in patients with ischemic and nonischemic cardiomyopathy. Heart Rhythm. 2010; 7:74-80.

Das M, Suszko AM, Nayyar S, Viswanathan K, Spears DA, Tomlinson G, Pinter A, Crystal E, Dalvi R, Krishnan S, Chauhan VS. Automated Quantification of Low-Amplitude Abnormal QRS Peaks From High-Resolution ECG Recordings Predicts Arrhythmic Events in Patients With Cardiomyopathy. Circ Arrhythm Electrophysiol. 2017; 10:e004874.

Dizon J, Horn E, Neglia J, Medina N, Garan H. Loss of left bundle branch block following biventricular pacing therapy for heart failure: evidence for electrical remodeling? J Interv Card Electrophysiol. 2004; 10:47-50.

Gold MR, Birgersdotter-Green U, Singh JP, Ellenbogen KA, Yu Y, Meyer TE, Seth M, Tchou PJ. The relationship between ventricular electrical delay and left ventricular remodelling with cardiac resynchronization therapy. Eur Heart J. 2011;32:2516-2524.

Hawkins NM, Petrie MC, MacDonald MR, Hogg KJ, McMurray JJ. Selecting patients for cardiac resynchronization therapy: electrical or mechanical dyssynchrony? Eur Heart J. 2006; 27:1270-1281.

Igarashi M, Tada H, Yamasaki H, Kuroki K, Ishizu T, Seo Y, Machino T, Murakoshi N, Sekiguchi Y, Noguchi Y, Nogami A, Aonuma K. Fragmented QRS Is a Novel Risk Factor for Ventricular Arrhythmic Events After Receiving Cardiac Resynchronization Therapy in Nonischemic Cardiomyopathy. J Cardiovasc Electrophysiol. 2017; 28:327-335.

Karaca O, Cakal B, Omaygenc MO, Gunes HM, Cakal SD, Kizilirmak F, Gokdeniz T, Barutcu I, Boztosun B, Kilicaslan F. Native Electrocardiographic QRS Duration after Cardiac Resynchronization Therapy: The Impact on Clinical Outcomes and Prognosis. J Card Fail. 2016; 22:772-80.

Khan FZ, Virdee MS, Palmer CR, Pugh PJ, O'Halloran D, Elsik M, Read PA, Begley D, Fynn SP, Dutka DP. Targeted left ventricular lead placement to guide cardiac resynchronization therapy: the TARGET study: a randomized, controlled trial. J Am Coll Cardiol. 2012; 59:1509-1518.

Kosinski AS. A weighted generalized score statistic for comparison of predictive values of diagnostic tests. Stat Med. 2013; 32:964-77.

Lang RM, Badano LP, Mor-Avi V, Afilalo J, Armstrong A, Ernande L, Flachskampf FA, Foster E, Goldstein SA, Kuznetsova T, Lancellotti P, Muraru D, Picard MH, Rietzschel ER, Rudski L, Spencer KT, Tsang W, Voigt JU. Recommendations for cardiac chamber quantification by echocardiography in adults: an update from the American Society of Echocardiography and the European Association of Cardiovascular Imaging. J Am Soc Echocardiogr. 2015; 28:1-39.

Leyva F, Nisam S, Auricchio A. 20 years of cardiac resynchronization therapy. J Am Coll Cardiol. 2014; 64:1047-1058.

Rickard J, Zardkoohi O, Popovic Z, Verhaert D, Sraow D, Baranowski B, Martin DO, Grimm RA, Chung MK, Tchou P, Lindsay BA, Wilkoff BL. QRS fragmentation is not associated with poor response to cardiac resynchronization therapy. Ann Noninvasive Electrocardiol. 2011; 16:165-171.

Rickard J, Baranowski B, Grimm RA, Niebauer M, Varma N, Tang WHW, Wilkoff BL. Left Ventricular Size does not Modify the Effect of QRS Duration in Predicting Response to Cardiac Resynchronization Therapy. Pacing Clin Electrophysiol. 2017; 40:482-487.

Russo AM et al. ACCF/HRS/AHA/ASE/HFSA/SCAI/SCCT/SCMR 2013 appropriate use criteria for implantable cardioverter-defibrillators & cardiac resynchronization therapy: a report of the American College of Cardiology Foundation appropriate use criteria task force, Heart Rhythm Society, American Heart Association, American Society of Echocardiography, Heart Failure Society of America, Society for Cardiovascular Angiography & Interventions, Society of Cardiovascular Computed Tomography, & Society for Cardio M R. J Am Coll Cardiol. 2013; 61:1318-1368.

Cvijic M, Zizek D, Antolic B, Zupan I. Time Course of Electrical Remodeling of Native Conduction After Cardiac Resynchronization Therapy and Its Impact on Clinical Outcome. J Card Fail. 2017; 23: 257-261.

Sebag FA, Martins RP, Defaye P, Hidden-Lucet F, Mabo P, Daubert JC, Leclercq C. Reverse electrical remodeling by cardiac resynchronization therapy: prevalence and clinical impact. J Cardiovasc Electrophysiol. 2012; 23:1219-27.

Sinha SK, Bhagat K, Asif M, Singh K, Sachan M, Mishra V, Afdaali N, Jha MJ, Kumar A, Singh S, Sinha R, Khanra D, Thakur R, Varma CM, Krishna V, Pandey U. Fragmented QRS as a Marker of Electrical Dyssynchrony to Predict Inter-Ventricular Conduction Defect by Subsequent Echocardiographic Assessment in Symptomatic Patients of Non-Ischemic Dilated Cardiomyopathy. Cardiology Res. 2016; 7:140-145.

Tigen K, Karaahmet T, Gurel E, Cevik C, Nugent K, Pala S, Tanalp AC, Mutlu B, Basaran Y. The utility of fragmented QRS complexes to predict significant intraventricular dyssynchrony in nonischemic dilated cardiomyopathy patients with a narrow QRS interval. Can J Cardiol. 2009; 25:517-522.

International Search Report and Written Opinion dated Jul. 4, 2019 in related International Patent Application No. PCT/CA2019/050563 (8 pages).

Vanderheyden et al., "Myocardial gene expression in heart failure patients treated with cardiac resynchronization therapy responders versus nonresponders", J. Am. Coll. Cardiol., 2008, 51(2):129-136.

Al Hebaishi et al., "Predictors of Cardiac Resynchronization Therapy Response: The Pivotal Role of Electrocardiogram", The Scientific World Journal, Mar. 20, 2013, 2013: 837086 (pp. 1-6).

Rickard et al., "QRS fragmentation is not associated with poor response to cardiac resynchronization therapy", Ann Noninvasive Electrocardiol., 2011, 16(2): 165-171.

Cintron et al., "Prognostic significance of serial changes in left ventricular ejection fraction in patients with congestive heart failure", The V-HeFT VA Cooperative Studies Group, Circulation, 1993; 87(6 Suppl): VI17-23.

* cited by examiner

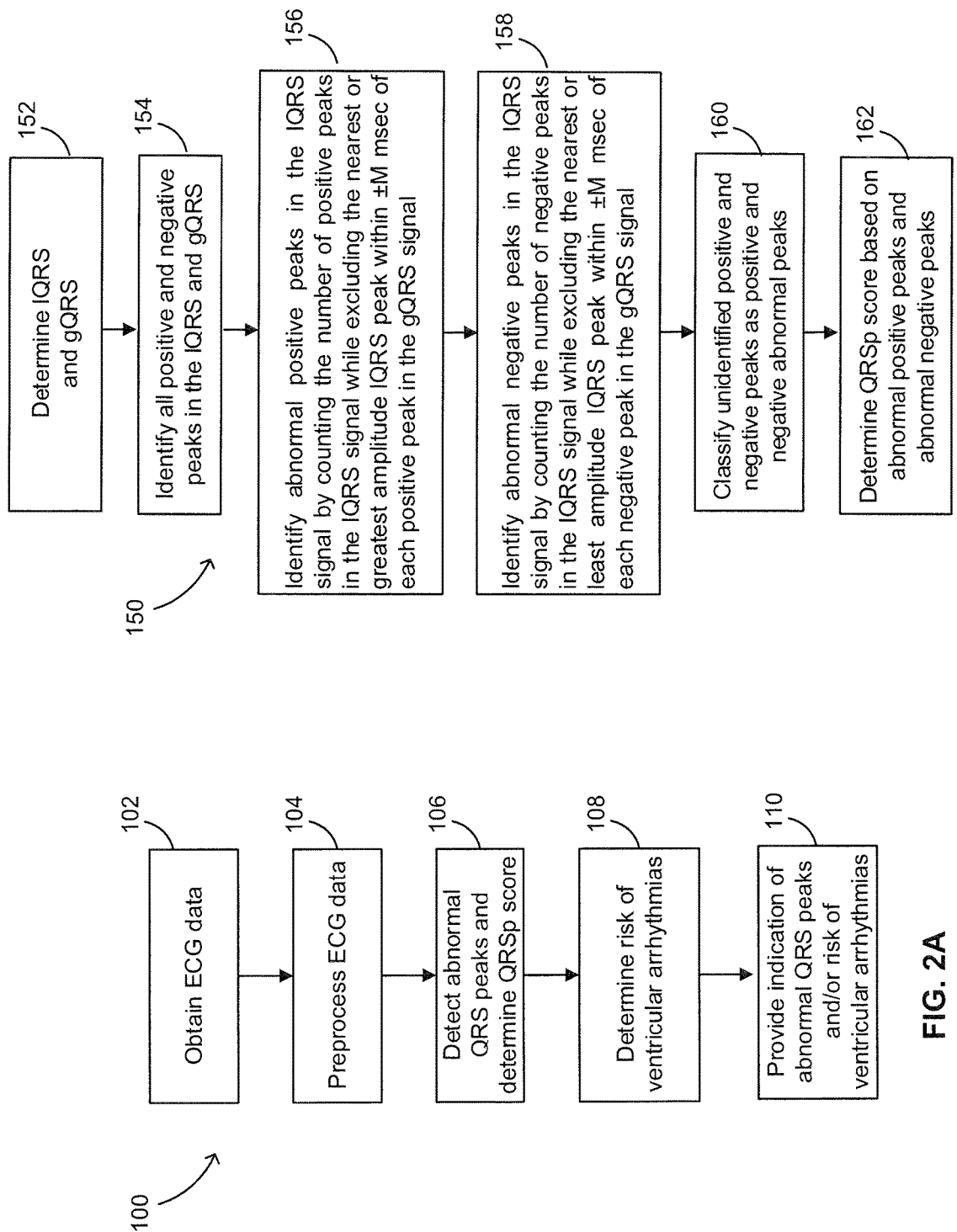

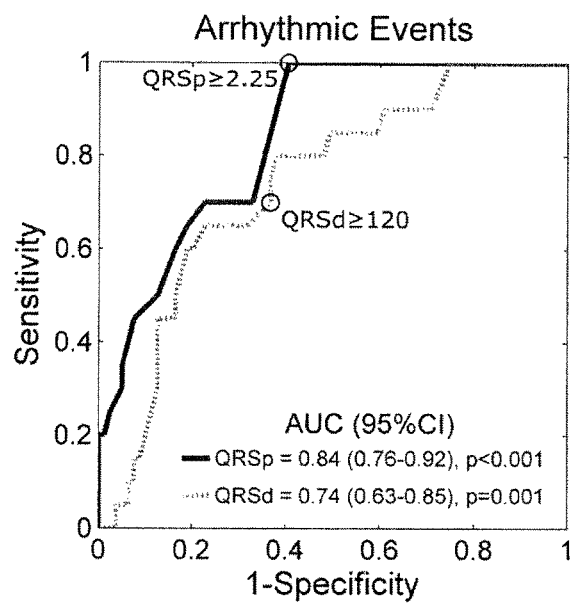
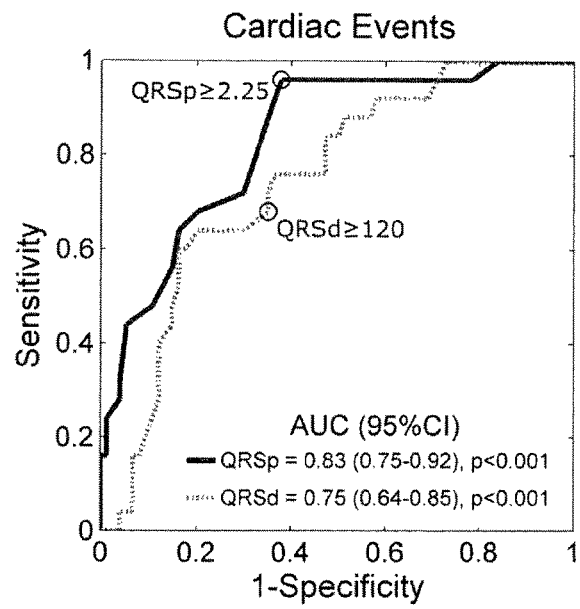
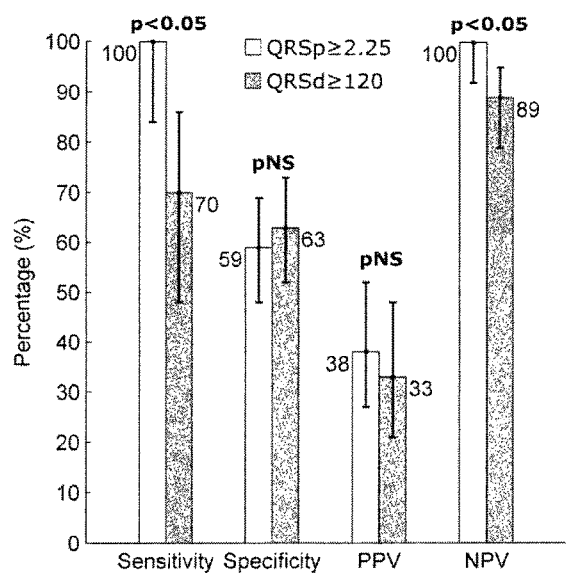
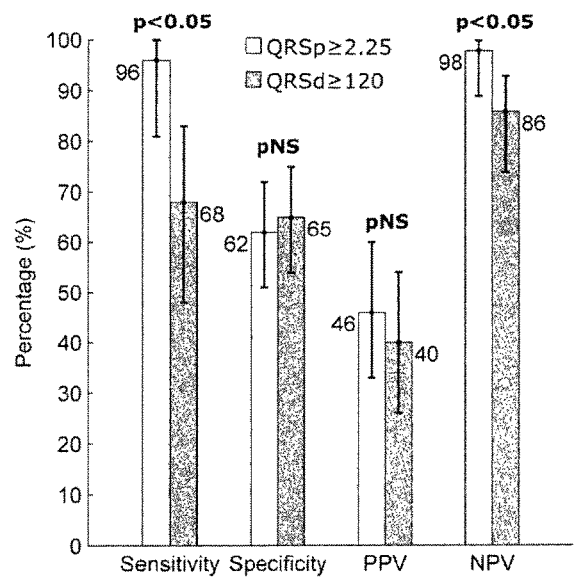
FIG. 8A  FIG. 8B

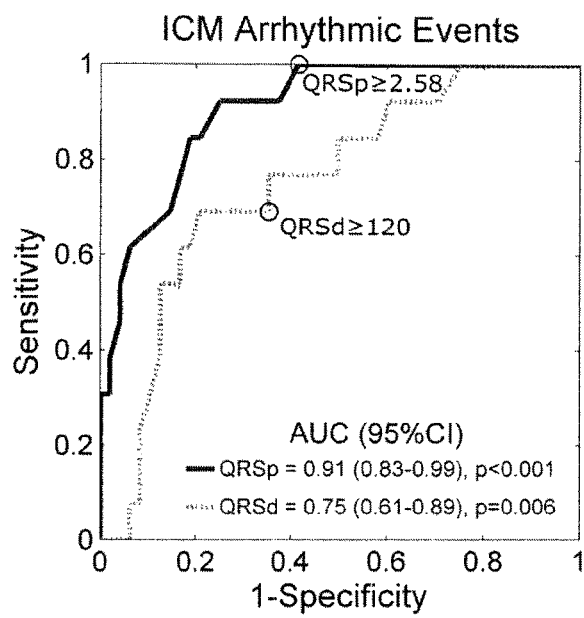
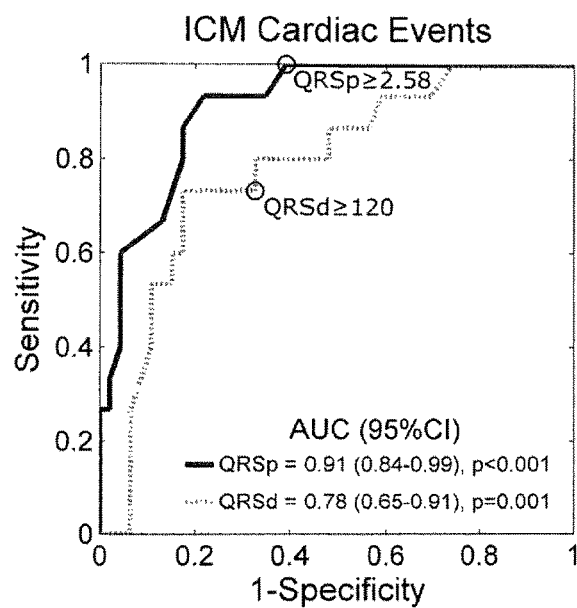
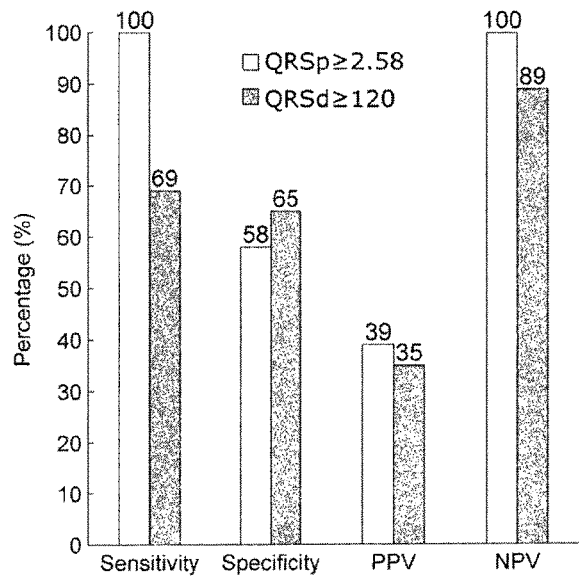
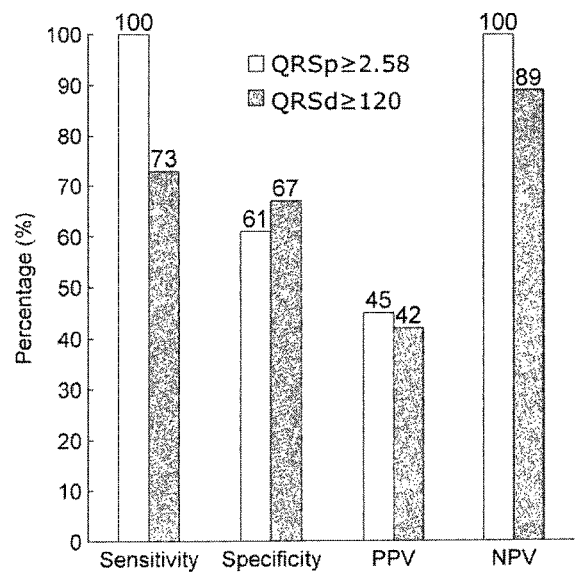
FIG. 15A
FIG. 15B

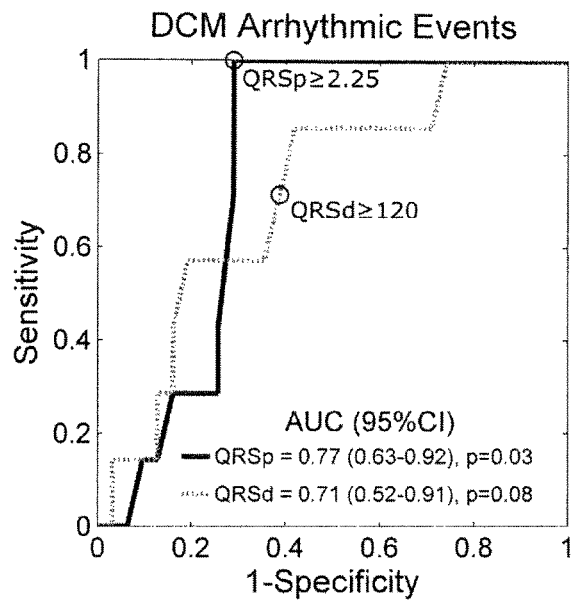
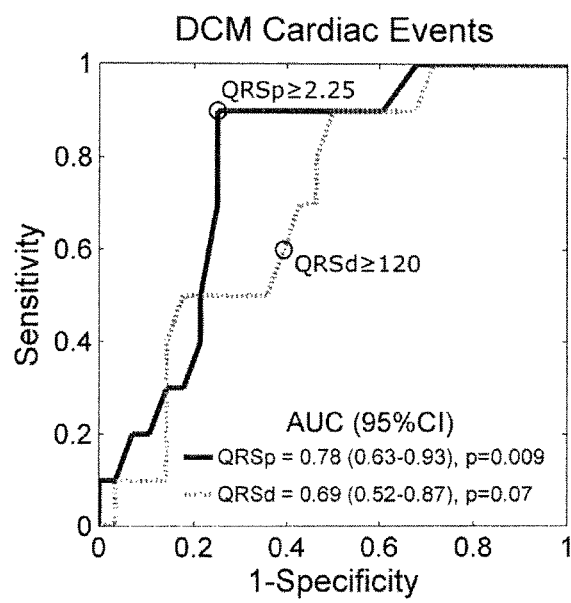
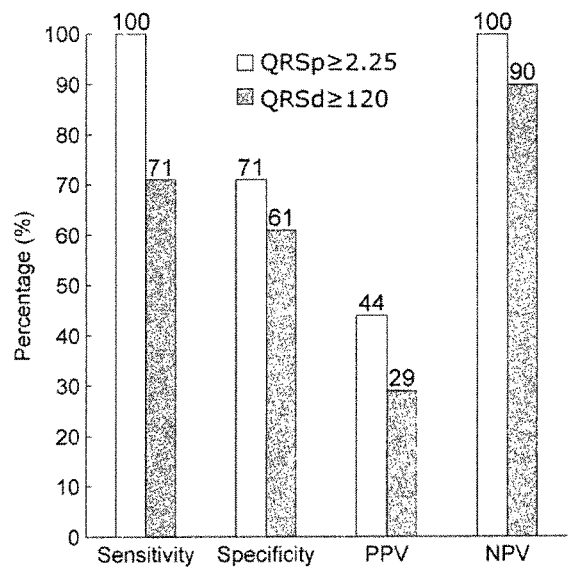
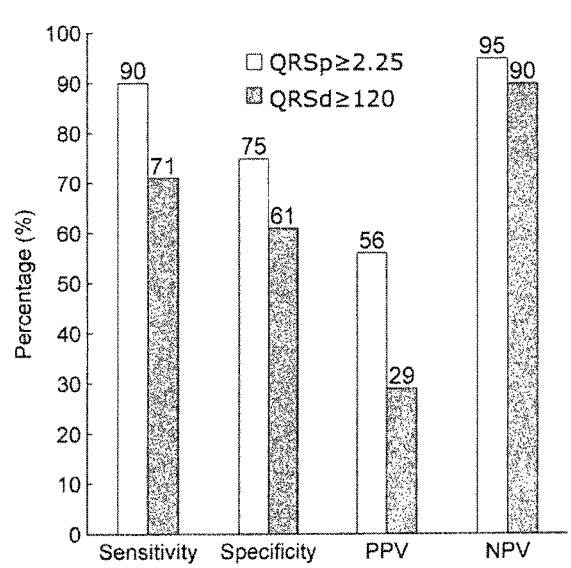
FIG. 17A  FIG. 17B

METHOD AND SYSTEM FOR ASSESSING QRS COMPONENTS AND THE RISK OF VENTRICULAR ARRHYTHMIAS

CROSS-REFERENCE TO RELATED APPLICATION

This application claims the benefit of U.S. Provisional Patent Application No. 62/164,046 filed May 20, 2015; the entire contents of Patent Application No. 62/164,046 are hereby incorporated by reference.

FIELD

Various embodiments are described herein that generally relate to a system and method for assessing QRS components and the risk of ventricular arrhythmias in various individuals.

BACKGROUND

Sudden cardiac death is the leading cause of death in North America. Sudden cardiac death can be caused by regional conduction delay in the heart which provides the electrical substrate for re-entrant ventricular tachyarrhythmias (VA). Regional conduction delay can produce fractionation in the surface electrocardiogram (ECG) QRS complex, which manifests as small notches, slurs or peaks [1]. Methods to quantify these abnormal QRS components have the potential to identify regional conduction delay and therefore discriminate patients at risk of ventricular arrhythmias and sudden cardiac death.

SUMMARY OF VARIOUS EMBODIMENTS

In a broad aspect, at least one embodiment described herein provides a method of assessing a risk of ventricular arrhythmias for a patient, wherein the method may comprise receiving ECG data obtained from the patient; analyzing the ECG data to detect abnormal QRS peaks; determining the risk of ventricular arrhythmias for the patient based on the detected abnormal QRS peaks; and providing an indication of the risk of ventricular arrhythmias for the patient.

In at least some embodiments, the method may comprise acquiring the ECG data from the patient using one or more ECG recording leads.

In at least some embodiments, the method may comprise preprocessing the ECG data. In such embodiments, the preprocessing of the ECG data may comprise applying a QRS template and optionally applying filtering.

In at least some embodiments, the ECG data may be high resolution data that was obtained using a sampling rate of at least 1,000 Hz.

In at least some embodiments, the method may comprise obtaining the ECG data from a data store, the ECG data having already been preprocessed.

In at least some embodiments, the act of analyzing the ECG data from a given ECG recording lead may comprise generating a local QRS (IQRS) signal from X beats of ECG data; generating a global QRS (gQRS) signal from Y beats of ECG data, where X and Y are integers and the X beats of ECG data are contained in the Y beats of ECG data; and comparing the IQRS signal with the gQRS signal to detect the abnormal QRS peaks in the IQRS signal.

In at least some embodiments, the IQRS signal may be generated by applying time averaging to unfiltered X beats of preprocessed ECG data, and the gQRS signal may be generated by filtering the Y beats of preprocessed ECG data using a smoothing filter and then applying time averaging to the filtered Y beats of ECG data, where the X beats of ECG data is a short data window and the Y beats of ECG data is a larger data window that is at least one order of magnitude larger than the short data window.

In at least some embodiments, the comparing may comprise identifying positive and negative peaks in the IQRS and gQRS signals; determining abnormal positive peaks in the IQRS signal by counting the number of positive peaks in the IQRS signal while excluding the nearest or greatest amplitude IQRS peak within $\pm M$ msec of each positive peak in the gQRS signal; determining abnormal negative peaks in the IQRS signal by counting the number of negative peaks in the IQRS signal while excluding the nearest or least amplitude IQRS peak within $\pm M$ msec of each negative peak in the gQRS signal; and determining a QRS peak (QRSp) score based on the total determined abnormal positive peaks and the abnormal negative peaks in the IQRS signal.

In at least some embodiments, the method may further comprise determining the IQRS signal using a sliding average of X beats of ECG data within the Y beats of ECG data and determining a set of QRSp scores for each set of averaged X beats of ECG data.

In at least some embodiments, the QRSp score for the given ECG recording lead may be an average, median or maximum of the set of QRSp scores derived from the given ECG recording lead.

In at least some embodiments, the QRSp score for the patient may be an average, median or maximum of the QRSp scores for ECG data obtained from at least a portion of the ECG recording leads.

In at least some embodiments, the act of determining the risk of ventricular arrhythmia for a given patient may comprise defining a quantitative risk measure associated with the QRSp score for the patient based on a multivariable regression model that is generated based on QRSp scores determined for healthy subjects, patients with heart disease but no ventricular arrhythmias and patients with heart disease in whom ventricular arrhythmias have occurred.

In at least some embodiments, the ECG data may comprise several sets of ECG data obtained using different ECG leads and the QRSp score is determined for each set of ECG data.

In another broad aspect, at least one embodiment described herein provides a system for assessing risk of ventricular arrhythmias for a patient, wherein the system may comprise an input interface for receiving ECG data obtained from the patient; an output interface for providing an indication of the risk of ventricular arrhythmia for the patient; and a processing unit coupled to the input and the output interfaces, the processing unit being configured to analyze the ECG data to detect abnormal QRS peaks; determine the risk of ventricular arrhythmia for the patient based on detected abnormal QRS peaks; and to provide the indication of the risk of ventricular arrhythmia for the patient using the output interface.

In at least some embodiments, the system may further comprise a sensor unit comprising sensors for sensing ECG data from the patient during use and a data acquisition unit coupled to the sensor unit and the processing unit for acquiring the sensed ECG data.

In at least some embodiments, the processing unit may be configured to perform any of the methods described in accordance with the teachings herein.

In another broad aspect, at least one embodiment described herein provides a computer readable medium comprising a plurality of instructions that are executable on a processing unit of a device for adapting the device to implement a method of assessing risk of ventricular arrhythmias for a patient, wherein the method may be defined in accordance with the teachings herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 2A is a flowchart of an example embodiment of a method for analyzing cardiac signals to assess risk of ventricular arrhythmias.

FIG. 2B is a flowchart of an example embodiment of a method for detecting abnormal QRS peaks (QRSp).

FIGS. 8A-8B show the performance of QRSp Mean and QRSd in predicting arrhythmic and cardiac events in the clinical study.

FIGS. 15A-15B show the performance of QRSp and QRSd in predicting arrhythmic and cardiac events in patients with ICM in the clinical study.

FIGS. 17A-17B show the performance of QRSp Mean and QRSd in predicting arrhythmic and cardiac events in patients with DCM in the clinical study.

Figure 1:
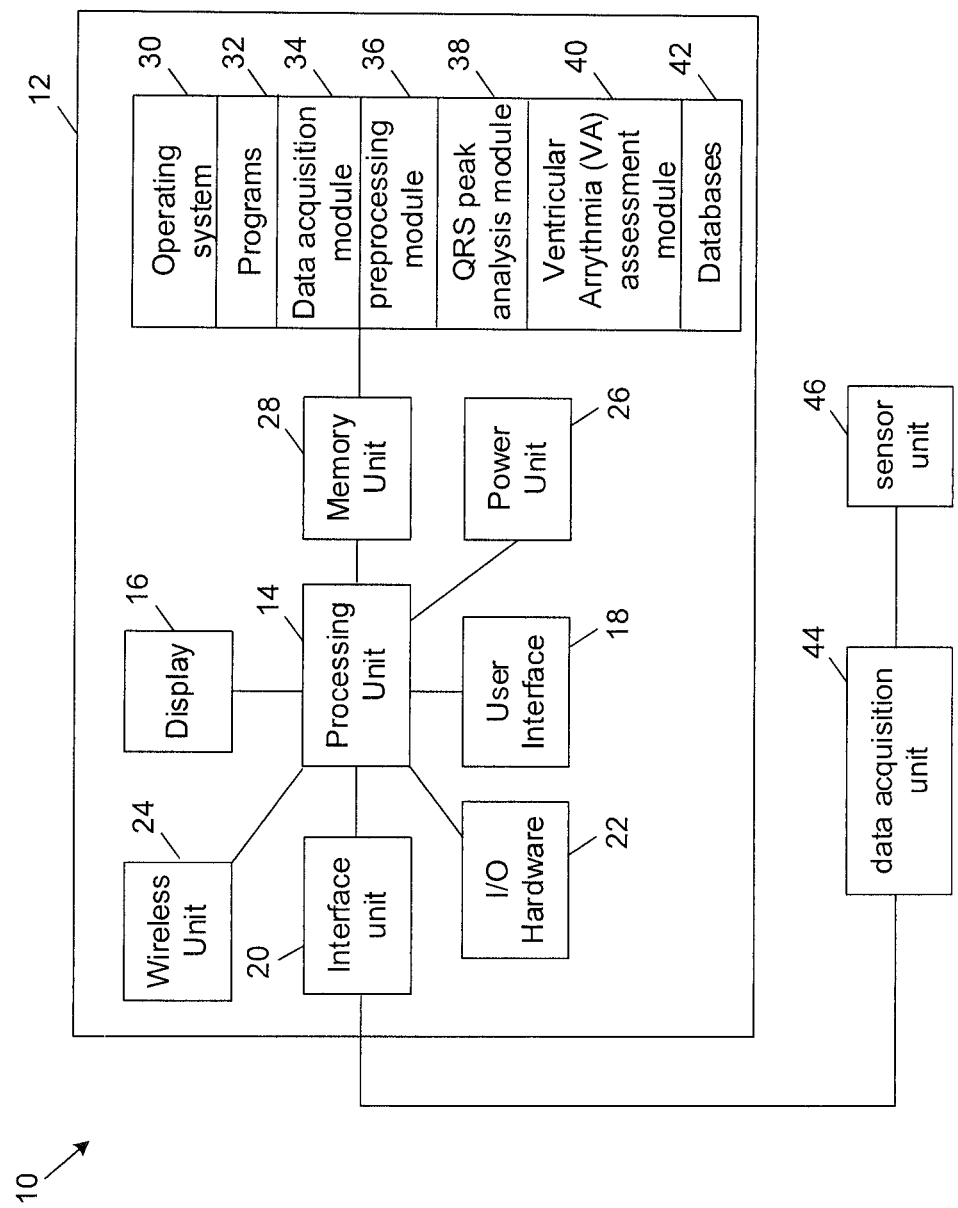
FIG. 1 is a block diagram of an example embodiment of a system for analyzing cardiac signals.

Further aspects and features of the example embodiments described herein will appear from the following description taken together with the accompanying drawings.

DETAILED DESCRIPTION OF THE EMBODIMENTS

Various systems, devices or methods will be described below to provide an example of at least one embodiment of the claimed subject matter. No embodiment described herein limits any claimed subject matter and any claimed subject matter may cover systems, devices or methods that differ from those described herein. The claimed subject matter is not limited to systems, devices or methods having all of the features of any one process or device described below or to features common to multiple or all of the systems, devices or methods described herein. It is possible that a system, device or method described herein is not an embodiment of any claimed subject matter. Any subject matter that is disclosed in a system, device or method described herein that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending on the context in which these terms are used. For example, the terms coupled or coupling can have a mechanical, electrical or communicative connotation. For example, as used herein, the terms coupled or coupling can indicate that two or more elements or devices can be directly connected to one another or connected to one another through one or more intermediate elements or devices via an electrical element, electrical signal or a mechanical element depending on the particular context. Furthermore, the term "communicative coupling" indicates that an element or device can electrically, optically, or wirelessly send data to or receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 10%, for example.

The example embodiments of the systems, devices or methods described in accordance with the teachings herein may be implemented as a combination of hardware or software. For example, the embodiments described herein may be implemented, at least in part, by using one or more computer programs, executing on one or more programmable devices comprising at least one processing element, and at least one data storage element (including volatile and non-volatile memory and/or storage elements). These devices may also have at least one input device (e.g. a keyboard, a mouse, a touchscreen, and the like), and at least one output device (e.g. a display screen, a printer, a wireless radio, and the like) depending on the nature of the device.

It should also be noted that there may be some elements that are used to implement at least part of the embodiments described herein that may be implemented via software that is written in a high-level procedural language such as object oriented programming. The program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a computing device that is readable by a general or special purpose programmable device having a processor, an operating system and the associated hardware and software that is necessary to implement the functionality of at least one of the embodiments described herein. The software program code, when read by the computing device, configures the computing device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Conventional methods to quantify abnormal QRS components to identify regional conduction delay and therefore discriminate patients at risk of ventricular arrhythmias have two limitations. First, the slurred components of the QRS, that do not produce actual peaks, may be overvalued. Conduction delays producing slurs may be less arrythmogenic than those associated with peaks. Second, transient QRS peaks may be undervalued as a consequence of long duration signal averaging which gives them the appearance of slurs. These transient QRS peaks can arise from small displacements of the recording ECG leads on the chest wall during respiration, which can subtly change the QRS morphology [2]. These limitations in combination may contribute to the poor sensitivity of conventional methods for identifying cardiac patients at risk of ventricular arrhythmias [3, 4] and cardiac death [5].

To address these limitations, at least one example embodiment of a novel time-domain based method that quantifies abnormal QRS peaks using a shorter averaging window in accordance with the teachings herein is described. The methods may be more selective in identifying abnormal QRS peaks which deviate from the intrinsic shape of the QRS complex and which are more likely to indicate arrhythmogenicity. By considering peaks and not slurs, the methods described herein may be more selective in identifying abnormal QRS components that deviate from the intrinsic shape of the QRS complex. Furthermore, by using averages based on a smaller number of beats such as, but not limited to, using a 10 to 50-beat average, the methods described herein may be more sensitive to identifying peaks that would otherwise be lost using a larger time averaging window. Accurate risk assessment is essential in cardiac patients to direct life-saving therapy such as costly implantable defibrillators.

In at least some embodiments, the detection of abnormal peaks in the QRS complex may be done automatically.

In at least some embodiments, the shorter beat averages may be unfiltered. For example, it may be possible to use unfiltered data that is captured in a low noise environment. However, this is not always possible and a minimal amount of filtering to reduce noise during the preprocessing stage may be used.

As described herein, a simulation was performed using synthetic QRS peaks to assess the robustness to noise of the methods described herein. The performance of the methods described herein was also tested using high-resolution precordial lead electrocardiograms recorded from normal subjects and patients with cardiomyopathy. In an example assessment, the 10-beat average performance was compared to a 100-beat average and shown to be more sensitive in detecting abnormal QRS peaks. An average of at least 100 beats is used in conventional QRS component algorithms depending on the amount of noise in the recorded data. Clinical performance was also tested in two clinical studies of cardiomyopathy patients and the methods described herein were shown to discriminate those at risk of ventricular arrhythmias with high sensitivity and specificity in these studies.

Referring now to FIG. 1, shown therein is a block diagram of an example embodiment of a cardiac risk assessment system 10 that may be used to analyze cardiac signals to assess risk of ventricular arrhythmia for a patient. The cardiac risk assessment system 10 includes an operator unit 12 that has at least one input for receiving cardiac electrical data, at least one processing unit for processing the cardiac electrical data to determine the electrical substrate and the risk of ventricular arrhythmias, and at least one output for providing an indication of electrical substrate and the risk of ventricular arrhythmias.

The cardiac risk assessment system 10 is provided as an example and there may be other embodiments of the system 10 with different components or a different configuration of the components described herein. The system 10 further includes several power supplies (not all shown) connected to various components of the treatment planning system 10 for providing power thereto as is commonly known to those skilled in the art.

In general, a user may interact with the operator unit 12 to analyze cardiac electrical data from a patient to determine whether there is a certain cardiac risk associated with the patient, such as a risk of ventricular arrhythmias. After the analysis, the user can then use the operator unit 12 to provide, display and/or store an indication of the cardiac risk. In some cases, the user may use the system 10 to obtain cardiac electrical data from the patient using appropriate sensors and data acquisition hardware and software.

The operator unit 12 comprises a processing unit 14, a display 16, a user interface 18, an interface unit 20, Input/Output (I/O) hardware 22, a wireless unit 24, a power unit 26, and a memory unit 28. The memory unit 28 comprises software code for implementing an operating system 30, various programs 32, a data acquisition module 34, a pre-processing module 36, a QRS peak analysis module 38, a ventricular arrhythmia (VA) assessment module 40, and one or more databases 42. Modules 34 to 40 will be described in greater detail with respect to FIGS. 2 to 6B. Some of the modules may be combined in some embodiments. Many components of the operator unit 12 can be implemented using a desktop computer, a laptop, a mobile device, a tablet, and the like.

In some embodiments, in which ECG data is to be obtained from a patient, the system 10 further comprises a data acquisition unit 44 and a sensor unit 46, which are described in further detail below.

The processing unit 14 controls the operation of the operator unit 12 and can be any suitable processor, controller or digital signal processor that can provide sufficient processing power depending on the configuration and operational requirements of the cardiac risk assessment system 10 as is known by those skilled in the art. For example, the processing unit 14 may be a high performance general processor. In alternative embodiments, the processing unit 14 may include more than one processor with each processor being configured to perform different dedicated tasks. In alternative embodiments, specialized hardware can be used to provide some of the functions provided by the processing unit 14.

The display 16 can be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or a handheld device such as an LCD-based display and the like.

The user interface 18 can include at least one of a mouse, a keyboard, a touch screen, a thumbwheel, a track-pad, a track-ball, a card-reader, voice recognition software and the like again depending on the particular implementation of the operator unit 12. In some cases, some of these components can be integrated with one another.

The interface unit 20 can be any interface that allows the operator unit 12 to communicate with other devices or systems. In some embodiments, the interface unit 20 may include at least one of a serial bus or a parallel bus, and a corresponding port such as a parallel port, a serial port or a USB port that provides USB connectivity. The busses may be external or internal. The busses may be at least one of a SCSI, USB, IEEE 1394 interface (FireWire), Parallel ATA, Serial ATA, PCIe, or InfiniBand. Other communication protocols may be used by the bus in other embodiments. The host interface component 134 may use these busses to connect to the Internet, a Local Area Network (LAN), a Wide Area Network (WAN), a Metropolitan Area Network (WAN), a Wireless Local Area Network (WLAN), a Virtual Private Network (VPN), or a peer-to-peer network, either directly or through a modem, router, switch, hub or other routing or translation device.

The I/O hardware 22 is optional and can include, but is not limited to, at least one of a microphone, a speaker, a keyboard, a mouse, a touch pad, a display device and a printer, for example.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 can include RAM, ROM, one or more hard drives, one or more flash drives or some other suitable data storage elements such as disk drives, etc. The memory unit 28 may be used to store the operating system 30 and programs 32 as is commonly known by those skilled in the art. For instance, the operating system 30 provides various basic operational processes for the operator unit 12. The programs 32 include various user programs so that a user can interact with the operator unit 12 to perform various functions such as, but not limited to, acquiring data, pre-processing data, analyzing preprocessed data, determining cardiac risk based on the analysis as well as viewing, manipulating, communicating and storing data as the case may be.

The databases 42 can be used to store data for the system 10 such as system settings, parameter values, and calibration data. The databases 42 can also store other information required for the operation of the programs 32 or the operating system 30 such as dynamically linked libraries and the like.

The data acquisition module 34 may be used to obtain cardiac electrical data (e.g. bipolar and unipolar body surface ECG, bipolar and unipolar intracardiac electrograms) from a patient. The preprocessing module 36 then preprocesses the cardiac electrical data so that it may be analyzed more accurately. The QRS peak analysis module 38 then analyzes the preprocessed cardiac electrical data to determine the abnormal QRS peaks. The ventricular arrhythmia (VA) assessment module 40 then determines a risk of ventricular arrhythmias based on the abnormal QRS peaks. The operation of the modules 34 to 40 will be discussed in more detail in relation to the description of FIGS. 2 to 6B. It should be noted that the various modules 34 to 40 may be combined or further divided into other modules. The modules 34 to 40 are typically implemented using software, but there may be some instances in which at least some of these modules are implemented using FPGA or application specific circuitry.

The databases 42 can be used to store data for the system 10 such as system settings, parameter values, and calibration data. The databases 42 may also be used to store other information required for the operation of the programs 32 or the operating system 30 such as dynamically linked libraries and the like. The databases 42 may also be used to store data on patients from which electrogram data has been obtained and the results of assessing cardiac risk.

The operator unit 12 comprises at least one interface that the processing unit 14 communicates with in order to receive or send information. This interface can be the user interface 18, the interface unit 20 or the wireless unit 24. For instance, the amount of cardiac electrical data, as well as the recording, processing and analysis parameters that may be used by the system 10 may be inputted by a user or otherwise selected through the user interface 18 or this information may be received through the interface unit 20 from a computing device. The processing unit 14 can communicate with either one of these interfaces as well as the display 16 or the I/O hardware 22 in order to use this input information to analyze cardiac electrical data obtained from a patient and in some cases to obtain and preprocess the cardiac electrical data from the patient. In addition, users of the operator unit 12 may communicate information across a network connection to a remote system for storage and/or further analysis of the trials and their associated simulation results in some embodiments.

A user can also use the operator unit 12 to provide information needed for system parameters that are needed for proper operation of the system 10 such as calibration information and other system operating parameters as is known by those skilled in the art. Data that is obtained from patients, as well as parameters used for operation of the system 10, may be stored in the memory unit 28. The stored data may include raw sampled data as well as processed cardiac electrical data, and/or analyzed data.

The data acquisition unit 44 comprises hardware circuitry that is needed to record cardiac electrical data from a patient. Different variations are possible for the data acquisition unit 44 as is known by those skilled in the art. For example, the data acquisition unit 44 may comprise a multi-channel digital data acquisition system with a controller and one or more data acquisition boards each having a certain number of recording channels. Each data acquisition board may generally comprise an amplifier bank, a filter bank, a multiplexer, an Analog to Digital Controller (ADC) and a DSP unit. The DSP unit may be implemented by one or more processors or by specialized circuitry as is known by those skilled in the art.

In use, data measured by a given recording channel is amplified by a corresponding amplifier in the amplifier bank, filtered by a corresponding filter in the filter bank, multiplexed by the multiplexer, and then digitized by the ADC. The individual gains of the amplifiers in the amplifier bank may be applied to groups of channels and may be automatically set by the processing unit 14 or an on-board DSP unit in the data acquisition unit 44 that receives commands from the operator unit 12 via a communication link (such as, but not limited to an RS-232 link, for example). Data and commands may be exchanged between the one or more acquisition boards and the processing unit 14 via one or more buses.

During data acquisition, the data acquisition unit 44 obtains cardiac electrical data and sends the cardiac electrical data through a link to the operator unit 12 for storage and analysis. A multiplexer circuit may be used to interface all of the data acquisition boards. The processor or on-board DSP unit may also control the data acquisition parameters (e.g. amplifier gains, filter coefficients, detection threshold and sampling sequence during data acquisition). Sampling rates may be set to at least 1,000 Hz and analog filters may be set to have a passband of about 0.05-400 Hz. In addition, amplifiers may be selected so that the common mode rejection ratio on the bipolar and unipolar channels is greater than about 90 dB from DC to 1,000 Hz, which is sufficient for 12 bit resolution. In some cases, the front end of the data acquisition unit 44 may be battery-operated, providing full electrical isolation.

The sensor unit 46 may be used to record cardiac signals, such as body surface ECG signals or intracardiac signals, from which ECG data is derived. The electrodes can be standard ECG electrodes, carbon electrodes, platinum electrodes, silver-silver chloride electrodes, or variations thereof. The electrodes can be configured in the standard 12-lead configuration or Frank lead vectorial configuration. Alternatively, the number of ECG electrodes and their body surface configuration can be varied, such as in multielectrode thorax body surface mapping. These electrode sensors can be configured to record body surface or intracardiac electrical potentials in either a bipolar or unipolar configuration.

Referring now to FIG. 2A, shown therein is a flowchart of an example embodiment of a method 100 for analyzing cardiac signals to determine a risk of ventricular arrhythmias. This may generally include obtaining and preprocessing ECG data, determining cardiac risk by analyzing the preprocessed ECG data to determine abnormal QRS peaks, and then providing an indication of the abnormal QRS peaks and/or the risk of ventricular arrhythmias.

In some embodiments, the number of abnormal QRSp can also be measured serially over time, such as days, months or years apart, to provide a measure of changing electrical substrate in a patient and hence changing risk of ventricular arrhythmias. Based on a threshold number of abnormal QRS peaks and/or a threshold change in the number of abnormal QRS peaks, therapeutic decisions can be made such as altering a patient's medications or instituting cardiac interventions such as cardiac surgery, percutaneous coronary intervention, catheter ablation and/or defibrillator therapy.

This analysis may be done for different portions of ECG readings obtained from different areas of the patient's body surface or heart. For example, QRS peak detection may be done in consecutive 10 to 50 beat windows and the number of abnormal QRS peaks (QRSp) in each ECG recording over a 100 to 500 beat recording sequence may be determined.

The cardiac risk assessment method 100 starts with obtaining ECG data at 102 in which the sensor unit 46 is applied to a patient or subject to measure ECG data using a plurality of leads placed on the body surface or within the heart. The data acquisition module 34 in combination with the data acquisition unit 44 and the sensor unit 46 may be used at 102. Unipolar lead configuration (e.g. precordial leads V1-V6) may be preferable since each is an independent recording. However, in alternative embodiments, a bipolar lead configuration may be used. The ECG data is obtained using a sufficient sampling rate and resolution to identify abnormal QRS peaks according to the teachings herein. For example, high resolution ECG data is preferable, which may be obtained using a sampling rate of at least 1,000 Hz.

At 104, the ECG data is preprocessed. The preprocessing may include using a QRS template matching stage followed by an ECG signal filtering stage. This processing may be done by the preprocessing module 36.

For example, in at least some embodiments, a QRS template may be constructed for each ECG recording lead by manually or automatically defining the QRS start and end points on a representative QRS complex (e.g. a QRS complex resulting from native or intrinsic electrical conduction of the heart as opposed to a QRS complex derived from a premature beat or fusion beat or artifact). In other embodiments, an automatic QRS start and end detector may be implemented. The earliest QRS onset found in any lead may be used as the template start point for each lead and the latest QRS offset found in any lead may be used as the template end point for each lead. The QRS template may be aligned and compared with each QRS complex to identify morphologically dissimilar beats (i.e. QRS beats arising from premature beats, fusion beats or artifacts) that are excluded from analysis. The R wave location of each QRS complex in the ECG may be identified using the Pan and Tompkins automated peak detection method [6], in at least some embodiments. However, other methods to identify R wave location may also be used in some embodiments, such as, but not limited to, one of wavelet transformation, neural networking, or dictionary-based comparative methods. For each beat in the ECG recording, which may be 3 minutes long for example, the R wave of the template may be aligned with the R wave of the individual beat. The alignment can be achieved using cross-correlation of a moving window that may be incremented by a single sample point from a certain time before to a certain time after the initial alignment position [7], such as 25 msec before to 25 msec after, for example. The temporal point that produces the greatest average correlation coefficient (between the QRS complexes and template) for all ECG leads is set as the optimal alignment position. Once QRS complexes are aligned, those QRS complexes that do not achieve a pre-specified cross-correlation with the template, such as >90%, on all ECG leads, are excluded from analysis because they do not sufficiently match the morphology of the template. This process may be repeated until a certain number of QRS complexes matching the template have been identified, such as 100 to 500 QRS complexes, for example. These template-matched QRS complexes are saved for further processing.

In at least some embodiments, the entire ECG recording may be filtered after template matching to further eliminate noise. For example, to attenuate high frequency noise, a lowpass filter may be applied to the ECG data after template matching. The lowpass filter may be a $4^{th}$ order (Butterworth) bidirectional lowpass filter with a 150 Hz cutoff frequency, for example, although others may be used.

In at least some embodiments, the ECG filtering may further include removing low frequency baseline wander by applying cubic spline correction [8]. Spline anchors may be placed in the isoelectric PR segment at a certain point prior to the aligned onset of each QRS complex, such as 15-25 ms, for example and preferably 20 ms. A cubic spline may then be fit to the anchor points and subtracted from the original ECG recordings to remove the baseline wander.

It should be noted that acts 102 and 104 may be optional in that the method 100 may be applied to ECG data that has already been obtained and preprocessed. In this case, the preprocessed ECG data is loaded from a data source, such as a data store, and the method starts at act 106.

At act 106, the method 100 comprises analyzing the preprocessed ECG data to detect abnormal QRS peaks, referred to hereafter as abnormal QRSp, that actually perturb the underlying QRS morphology and to determine scores for abnormal QRSp. This detection may be done for ECG data recorded from one ECG lead or multiple ECG leads. For example, scores for abnormal QRSp, hereafter referred to generally as QRSp scores may be determined. There are several different types of QRSp scores that may be determined as described below. For example, scores for abnormal QRSp may be separately determined for smaller time windows of ECG data for each lead, such as a 10 beat window, for example, where the smaller time window is slid along a larger time window having a larger number of beats, such as 100 beats, for example; in this case the abnormal QRSp score is a QRSp window (QRSpW) score. Each lead may then be assigned a QRSplead (QRSpL) score which may be the mean, median or maximum of the QRSp QRSpWscores determined for each of the smaller windows of ECG data for that lead. The final QRSp score (QRSpF) that may be used to determine VA risk for the patient or subject may be the QRSpL score from a single ECG lead, or may be based on a combination of the QRSpL scores from all or a subset of the ECG leads. The combination may be the mean, median or maximum QRSpL score across the ECG leads that are used for the QRSpF score. ECG data from a given lead may be chosen to determine the QRSpF score if the amount of noise in the ECG data for the given ECG lead is acceptable.

Figure 3A:
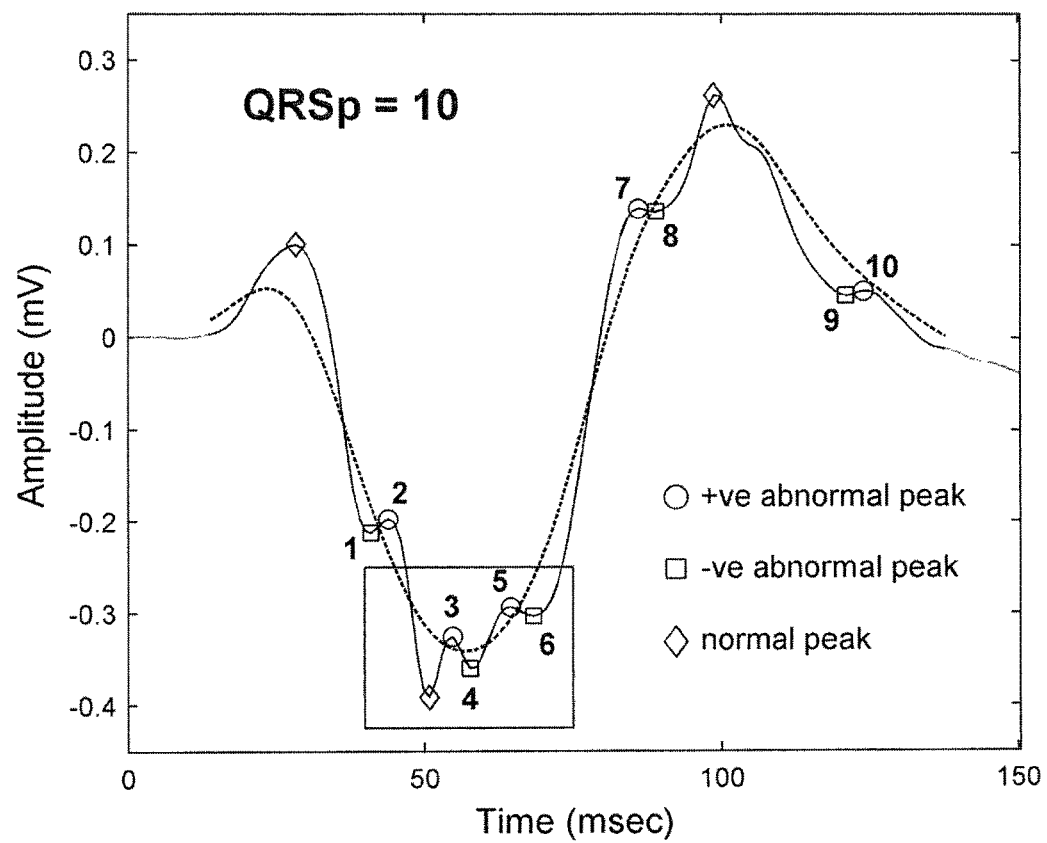
FIGS. 3A and 3B show detection of normal and abnormal QRS peaks from precordial electrocardiogram recordings in a patient with ischemic cardiomyopathy (ICM) using the teachings described herein.
Figure 3B:
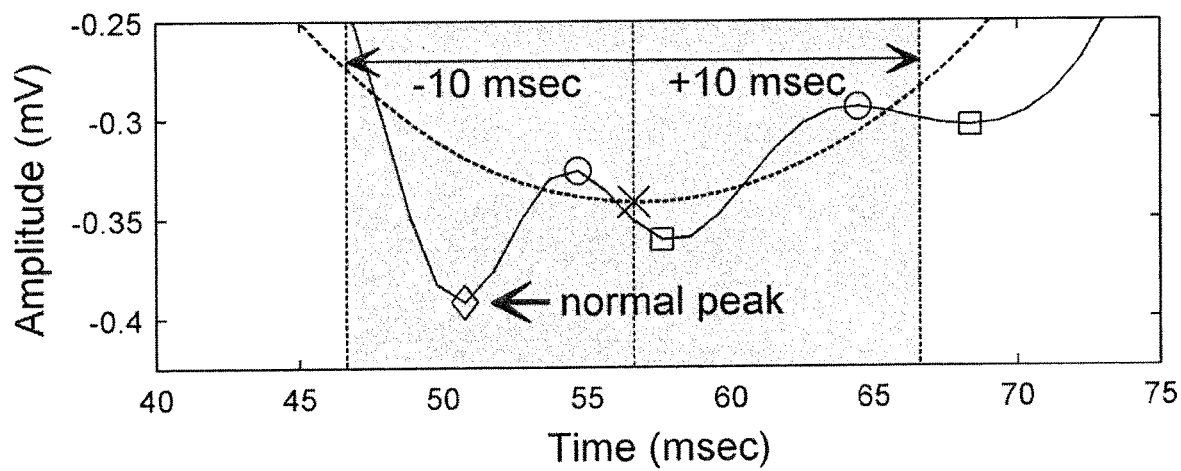

The detection of abnormal QRS peaks may be performed by the QRS peak analysis module 38. According to the teachings herein, abnormal QRSp may be distinguished from normal QRS peaks by comparing two preprocessed versions of the QRS complex, namely the local QRS average (lQRS) and the global QRS average (gQRS). The gQRS may be generated by applying a smoothing filter, such as a 15-point bidirectional moving average filter, for example, to the ECG data from a lead and then performing averaging on a plurality of filtered QRS complexes such as from Y beats of ECG data. Other smoothing filters may be used in alternative embodiments such as, but not limited to, median filters, low pass FIR filters (e.g. Butterworth, Chebyshev, etc.) or wavelet based filters. Typically, 100 to 500 filtered QRS complexes may be averaged, with 100 being preferable, for example. This produces the gQRS which is a smoothed QRS complex with low frequency contours, which constitutes the normal QRS peaks. The IQRS may be generated by averaging a smaller number of unfiltered consecutive QRS complexes such as from X beats of ECG data. Typically 10 to 50 unfiltered QRS complexes may be averaged, with 10 being preferable, to obtain the IQRS. Unfiltered in this context means that there is no additional filtering after the preprocessing of the ECG data. The parameters X and Y are integers and the X beats of ECG data are contained in the Y beats of ECG data. Since the IQRS is unfiltered, it will contain both normal QRS peaks and abnormal QRS peaks. As illustrated in FIGS. 3A and 3B, abnormal QRSp may be defined by comparing the IQRS signal with the gQRS signal to detect the abnormal QRS peaks in the IQRS signal which may be all of the peaks in the IQRS complex that are not in the gQRS complex. This may be repeated by sliding a window of X beats of ECG data within the larger window of Y beats of ECG data.

In some embodiments, the X and Y beats of ECG data may be continuous in time. Alternatively, in some embodiments, the X and Y beats of ECG data may not be continuous as at least one intermediate beat of ECG data may be discarded for having too much noise.

Referring now to FIG. 2B, shown therein is a flowchart of an example embodiment of a method 150 for detecting abnormal QRS peaks and quantifying a QRSpL score, which may be performed independently for each ECG recording lead. At 152, the IQRS signal and the gQRS signal are determined as explained above. The IQRS signal is a shorter local QRS average of the ECG data for a given recording ECG lead and the gQRS signal is a longer global QRS average of the ECG data for the given ECG recording lead.

At 154, the method 150 comprises identifying the set of all positive and negative peaks for the IQRS and the gQRS. A positive peak may be defined as any point where the preceding and subsequent ECG data samples have a lower amplitude than a current ECG data sample. A negative peak may be defined as any point where the preceding and subsequent ECG data samples have a greater amplitude than a current ECG data sample.

It should be noted that, in some instances, certain smoothing filters may produce a false gQRS peak (i.e. due to filter ringing) that has no true corresponding peak on the IQRS. Accordingly, a moving average filter may be used as it does not cause ringing. However, if another smoothing filter is applied (e.g. a wavelet-based filter), then a check may be performed to make sure that the gQRS peak is real. For example, for each positive and negative peak of the gQRS, a corresponding peak should exist on the non-smoothed 100-500 beat average. Any positive peak found on the gQRS that is not within ±Z msec (which may be considered to be a proximity window) of a positive peak of the non-smoothed average will be considered spurious and removed from the set of gQRS peaks. Any negative peak found on the gQRS that is not within ±Z msec (which may be considered to be a proximity window) of a negative peak of the non-smoothed average will be considered spurious and removed from the set of gQRS peaks. The parameter Z may be 10-20 msec, for example.

At 156, the method 150 comprises, for each positive gQRS peak, identifying the subset of positive IQRS peaks within IX msec (which may be considered to be a proximity window) of the gQRS peak location and classifying the IQRS peak with the most positive amplitude in the subset or the IQRS peak that is closest to the corresponding gQRS peak as a normal positive peak. The parameter X may be 10-20 msec and preferably 10 msec, for example.

At 158, the method 150 comprises, for each negative gQRS peak, identifying the subset of negative IQRS peaks found within ±Y msec (which may be considered to be a proximity window) of the gQRS peak location and classifying the IQRS peak with the most negative amplitude (in other words with the least amplitude) or the IQRS peak that is closest to the corresponding gQRS peak as a normal negative peak. The parameter Y may be 10-20 msec and preferably 10 msec, for example. In other embodiments, the parameters X and Y may have different values.

It should be noted that to determine which peak in the IQRS signal was a normal peak when there are multiple options within the proximity window one may: (1) choose the IQRS peak that is closest to the gQRS peak or (2) choose the IQRS peak that is of greatest magnitude. For example, if there are multiple negative IQRS peaks within close proximity to a negative gQRS peak (as in FIGS. 3A and 3B), only one of the peaks may be considered to be the normal peak. It was found that using either of the peak decision options (1) or (2), the resulting QRSp value that was determined was generally the same for both options.

At 160, the method 150 then comprises classifying the remaining unclassified positive IQRS peaks as positive abnormal peaks and the remaining unclassified negative IQRS peaks as negative abnormal peaks.

At 162, the method 150 then comprises determining a QRSp score based on the abnormal positive and abnormal negative IQRS peaks such as counting the total number of positive abnormal and negative abnormal IQRS peaks, for example.

The method 150 may be repeated for a set of consecutive short 10-50 beat ECG data windows that are incremented by a single beat from the first to the last of all of the 100-500 beats of ECG data to obtain a set of QRSpW scores. ECG data windows with a QRSpW score that occurs in fewer than N % of all windows, such as 5% for example, may be considered spurious and can be excluded from the subsequent QRSpL score calculations. The QRSpL score for each ECG lead may then be determined as the maximum, median or the mean QRSpW score across all 10-50 beat non-spurious data windows of that ECG lead (which are the same size as the data window used for the IQRS). In a similar manner, the QRSpL score may be independently determined for all remaining ECG leads. The risk of ventricular arrhythmias can be estimated from the QRSpF score, which may be the maximum, median or mean QRSpL scores from some or all of the ECG recording leads.

In an alternative embodiment, the act of determining the risk of ventricular arrhythmia for a given patient may comprise defining a quantitative risk measure associated with the QRSp score for the patient based on a multivariable regression model. Such a model may include QRSp scores from healthy subjects, patients with heart disease but no ventricular arrhythmias and patients with heart disease in whom ventricular arrhythmias have occurred. For example, this may be done using Cox multivariable modelling (see the Clinical Validation Study described herein including Table 5) to define a QRSp score Hazard Ratio that adjusts for the effect of other risk predictor variables. A patient's QRSp score in conjunction with the QRSp score Hazard ratio may then be used to quantify risk of ventricular arrhythmias.

Referring now to FIG. 3A, shown therein is an Illustration of the abnormal QRS detection method applied to precordial ECG lead V5 of an ischemic cardiomyopathy (ICM) patient. Five positive (shown by circles) and 5 negative (shown by squares) abnormal QRS peaks are identified on the local QRS (IQRS) (shown by a solid line) after identifying 3 normal peaks (shown by diamonds) using the smoothed global QRS (gQRS) (shown by a dashed line). The number of positive and negative abnormal peaks may be summed to produce a QRSpW score of 10 for a single 10-50 beat data window from lead V5. FIG. 3B is a magnified view of FIG. 3A, which illustrates an example of normal QRS peak classification. A negative peak is identified on the smoothed gQRS (at the position labelled 'x'). The most negative peak on the IQRS within a certain time window, such as but not limited to ±10-20 msec, of the gQRS peak may be classified as normal.

Figure 4:
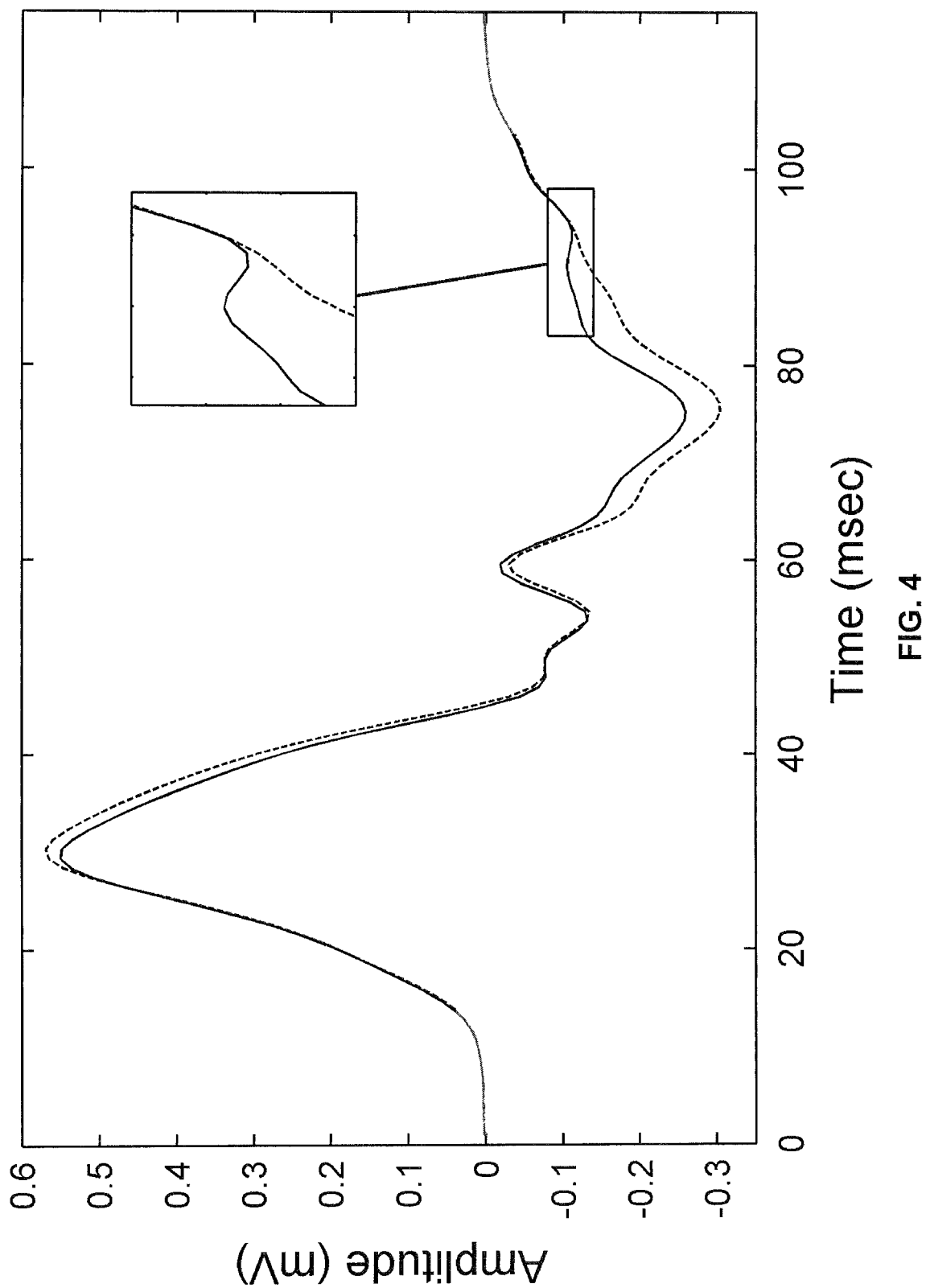
FIG. 4 shows an example of an unfiltered 10-beat QRS average (solid line) and an unfiltered 100-beat QRS average (dashed line) for a patient.

The aforementioned abnormal QRSp detection and quantification method may be applied to consecutive 10-50-beat data windows that are incremented by a single beat until the end of the 100-500 beat QRS data set. Averaging QRS complexes using a 10-50 beat moving data window may improve abnormal QRS peak detection as there is minimal respiratory chest wall movement during this brief period of time. Longer averaging windows that include multiple respiratory cycles may result in QRS peak underdetection because the QRS morphology can subtly change with movement of the chest wall [2]. This is illustrated in FIG. 4, which is an example comparing an unfiltered 10-beat QRS average (solid line) to an unfiltered 100-beat QRS average (dashed line) from precordial lead V4 of a representative patient. Although the two averaged beats appear similar, the inset clearly shows that a small abnormal QRS peak is present in the 10-beat average but not in the 100-beat average. By applying the 10-50 beat moving window analysis over 100-500 total beats, QRSp can be assessed over multiple respiratory cycles in order to derive the maximum number of abnormal QRS peaks. The duration of the shorter averaging window can be set to 2-50% of the total number of beats sampled and preferably 10%, for example depending on the amount of beats in the larger averaging window (e.g. 100-500 beats). If the larger averaging window has 500 beats, a 10-50 beat range may be set for the smaller averaging window which is 2-10% of the larger averaging window. However, if the larger averaging window is set at a minimum of 100 beats, a 10-50 beat range can be selected for the smaller averaging window which is 10-50% of the larger averaging window. Alternatively, in some embodiments, the duration of the smaller and larger averaging windows may be adjusted based on the patient's respiratory rate during the ECG recording. The respiratory rate can be determined from the low frequency content of the ECG recording evaluated by spectral analysis, such as Fourier transformation. In this way, the duration of the averaging windows can be dynamically adjusted if respiratory rate changes during the ECG recording. For instance, if the respiratory rate slows, then the smaller and larger averaging windows would increase in size.

Referring again to FIG. 2A, at 108, the risk of ventricular arrhythmias may be determined from the patient's QRSpF score, derived from analysis of all ECG leads. This may be performed by the ventricular arrhythmia assessment module 40 using a variety of different techniques. For example, experimental data may be obtained from patients who are normal, who have heart disease with a history of ventricular arrhythmias and who have heart disease without a history of ventricular arrhythmias from which QRSpF scores may be determined. A QRSp score hazard ratio for developing ventricular arrhythmias can be determined using multivariable regression analysis [9], which can control for the effects of other clinical variables, such as age, severity of heart disease, competing comorbidities, and other ECG metrics (such as QRS duration, etc) that have been associated with ventricular arrhythmias. When applied prospectively to a given cardiac patient, the QRSpF score hazard ratio in combination with the QRSpF score can provide a quantitative measure of individual ventricular arrhythmia risk. For example, a QRSpF score hazard ratio of X indicates that a patient's risk of ventricular arrhythmia increased X-fold for each abnormal QRSpF.

At 110, an indication of abnormal QRSp and/or risk of ventricular arrhythmias may be provided by displaying this information on the display 16 or saving this information in one of the databases 42. In some cases, a hardcopy report with this information may also be generated. Also, there may be some embodiments where this information is sent over the network to a physician or caregiver for the patient. As previously described, the number of abnormal QRSp can also be monitored by being measured serially over time, such as days, months or years apart, to provide a measure of changing electrical substrate in a patient and hence changing risk of ventricular arrhythmias. Based on a threshold number of abnormal QRS peaks and/or a threshold change in the number of abnormal QRS peaks, therapeutic decisions can be made such as altering a patient's medications or instituting cardiac interventions such as cardiac surgery, percutaneous coronary intervention, catheter ablation and/or defibrillator therapy.

Simulation Study

Figure 5A:
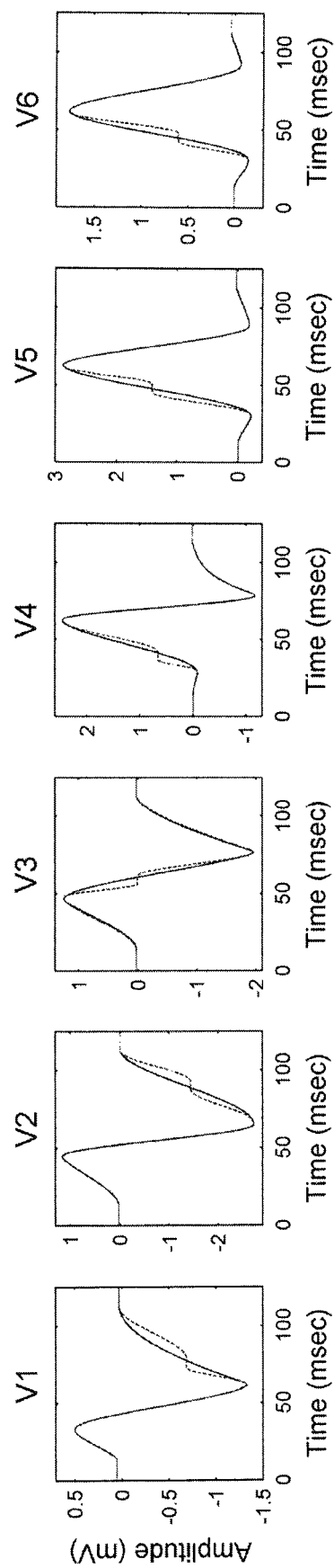
FIG. 5A shows simulated precordial QRS complexes with no added abnormal peaks (solid line) and a single added abnormal peak (dashed line).
Figure 5B:
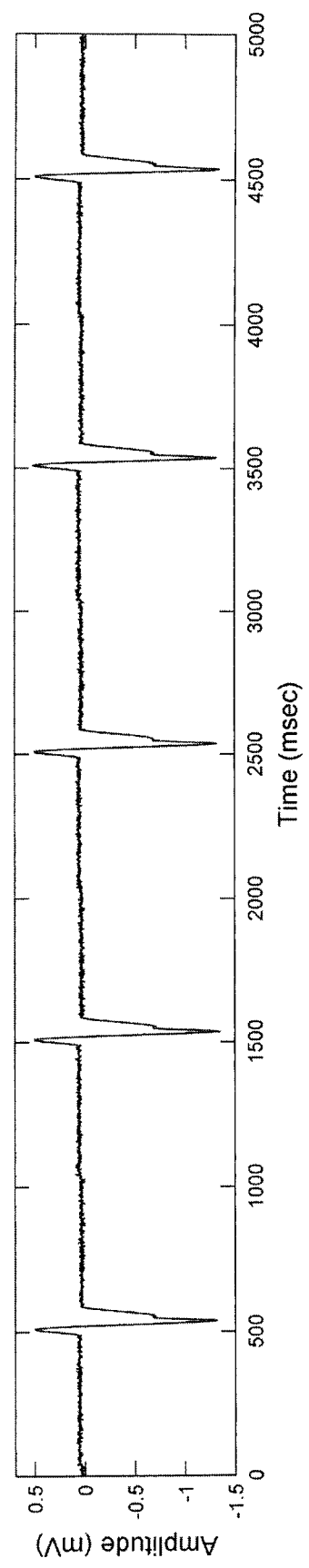
FIG. 5B shows a representative five beat segment from simulated ECG lead V1 with a single abnormal QRS peak and 40 μV of white noise.

A simulation study was conducted to evaluate the robustness of the abnormal QRS peak detection method to noise [10]. Two sets of QRS complexes were modelled using the precordial lead QRS complexes recorded from a normal subject with no intrinsic abnormal QRS peaks. The first set of simulated precordial QRS complexes included no abnormal QRS peaks and was modeled by fitting a cubic spline to a set of fiducial points corresponding to the start, end and peak points of the real QRS complexes. The second set of precordial QRS complexes was modeled in a similar manner but included the addition of one randomly positioned, small abnormal QRS peak (3 pV×5 msec). FIG. 5A shows the simulated precordial QRS complexes with no added abnormal peaks (solid line) and a single added abnormal peak (dashed line). Simulated ECGs were then constructed by repeating the simulated QRS complexes at 1,000 msec intervals. Multiple noisy ECGs were created by adding Gaussian white noise to the simulated ECG in increments of 5 pV from 0 to 100 pV. For example, FIG. 5B shows a representative five beat segment from simulated ECG lead V1 with a single abnormal peak and 40 pV of white noise.

The QRSp was analyzed at each noise level in 1,000 10-beat data windows incremented by a single beat from the first to the last beat of each simulated ECG. The noise level was measured for each beat (RMS-ST) by taking the root mean square of a highpass filtered ($4^{th}$ order Butterworth with 40 Hz cutoff) 40 msec portion of the ST segment beginning 20 msec after the end of the QRS [11].

The results of the simulation were used to determine an optimal noise cutoff for real world QRSp analysis, above which the detection of QRSp may be compromised. It was found that the filtering done for preprocessing did not affect QRSp detection as the QRSp detection method's accuracy was 100% with no added noise for both simulated ECG sets.

For the simulated ECG data set without the added QRS peak, false positive QRSp detections occurred with >50 pV added noise. For the simulated ECG data set with the added abnormal QRS peak, false positive and false negative QRSp detections occurred with >40 and >45 pV added noise, respectively. Based on the average RMS-ST value for all beats (12.5±1.4 pV) measured in the presence of 40 pV added noise, a conservative RMS-ST noise cutoff of 9.7 pV (2 standard deviations below mean) was selected for use with real world ECGs. Thus in the real world ECG analysis, QRS complexes that had an RMS-ST value>9.7 pV on any precordial lead may be excluded in order to avoid false QRS peak detection.

Retrospective Clinical Study

An embodiment of the QRSp method, in accordance with the teachings herein, was applied to normal subjects and ischemic cardiomyopathy (ICM) patients with reduced left ventricular ejection fraction (i.e. <40%) [10]. The study included 8 normal subjects, 10 ICM patients with no history of VA (−VA) and 10 ICM patients with a history of VA (+VA). ECG data was recorded for 3 minutes from individuals at rest in the supine position using a high resolution 12-lead Holter monitor (CM 3000-12BT, Getemed, Germany) with a 0.05-120 Hz analog bandwidth, ±6 mV voltage range, 12-bit digital resolution and 1024 Hz digital sampling rate.

The QRSp detection and analysis method was applied to the 3 minute ECG recordings. One-hundred analyzable beats with noise<9.7 uV were obtained for all individuals. There was no correlation between RMS-ST noise level and QRSp for all precordial leads (V1: $r=-0.3$, $p=0.11$; V2: $r=-0.1$, $p=0.49$; V3: $r=0.1$, $p=0.82$; V4: $r=0.1$, $p=0.50$; V5: $r=-0.4$, $p=0.07$; V6: $r=-0.2$, $p=0.38$). Thus, noise was not a confounder in QRSp detection.

Figure 6B:
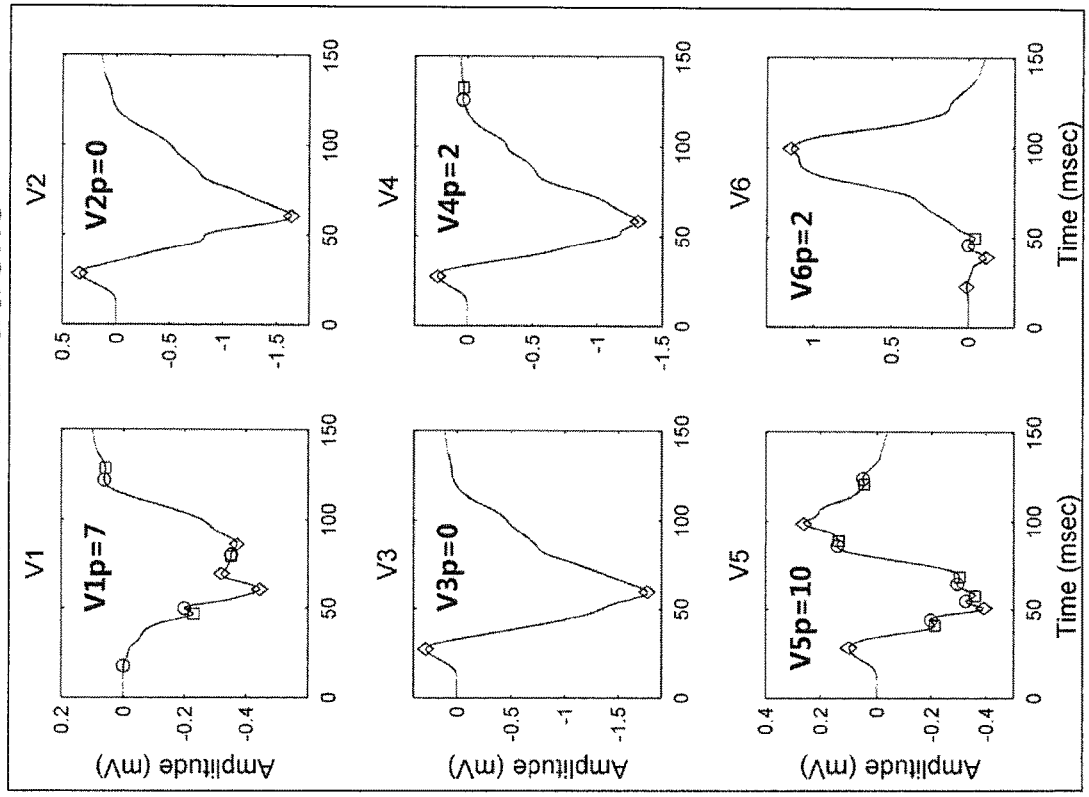
FIGS. 6A and 6B show total number of abnormal QRS peaks for each of the 6 precordial leads using the teachings described herein for a normal patient and an ICM +VA patient (i.e. an ICM patient with a history of ventricular arrhythmias (VA)).
Figure 6A:
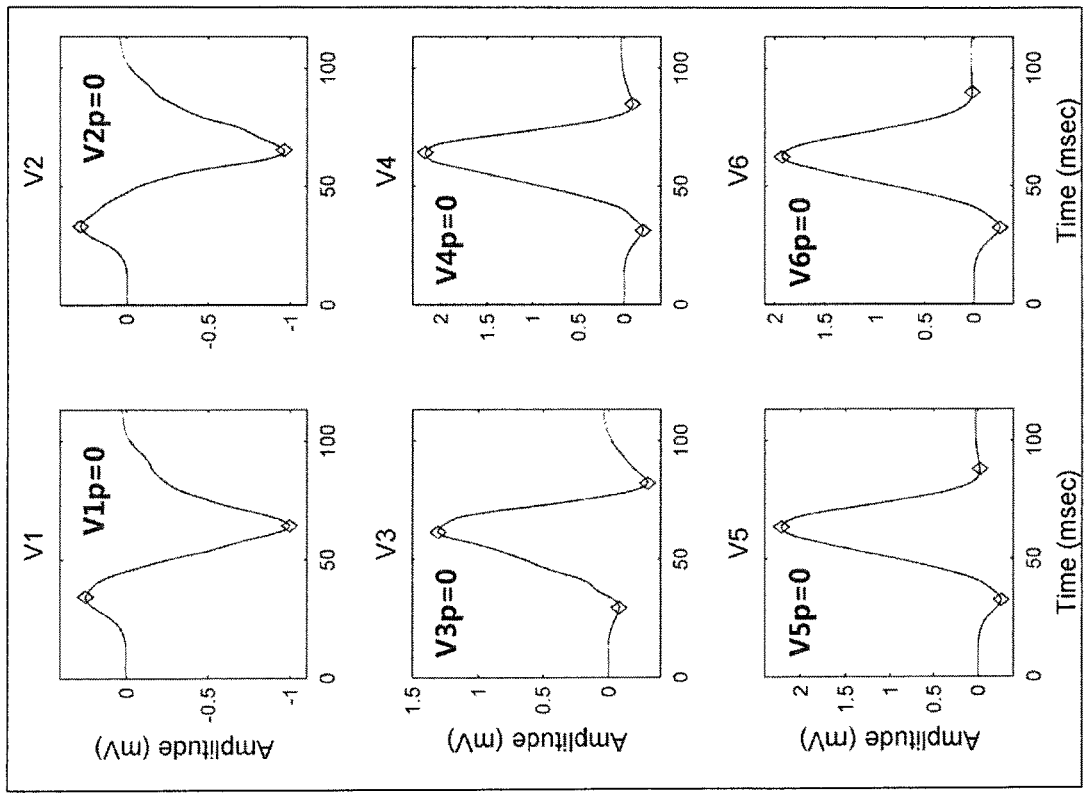

FIGS. 6A and 6B illustrate the QRSp results for a representative 10-beat window from a normal subject and an ICM +VA patient, respectively. In FIGS. 6A and 6B, normal peaks are annotated with diamonds, abnormal positive peaks are annotated with circles and abnormal negative peaks are annotated with squares. No QRSp was detected in any lead for the normal subject, which is anticipated when there is no heart disease. In contrast, QRSp was found in 4 of 6 precordial leads (i.e. V1, V4, V5 and V6) in the ICM +VA patient, with a maximum of QRSp of 10 detected in lead V5.

To determine the sensitivity of the QRSp detection and analysis method for identifying abnormal peaks, the maximum QRSp values from the 10-beat average moving window analysis was compared to the QRSp of the single 100-beat average. As shown in Table 1, the QRSp of the 10-beat average was significantly greater than the QRSp of the 100-beat average for all precordial leads. Thus, the shorter 10-beat average window was more sensitive in detecting QRSp.

TABLE 1

10-BEAT QRSp VS. 100-BEAT QRSp

| QRSp | 10-Beat Average | 100-Beat Average | P |
|---|---|---|---|
| V1p | 2 (0.5-4) | 2 (0-4) | 0.001* |
| V2p | 2 (0-2.8) | 2 (0-2) | 0.034* |
| V3p | 2 (0-4) | 2 (0-2) | 0.010* |
| V4p | 2 (0.3-3.5) | 2 (0-2) | 0.008* |
| V5p | 2 (0-4) | 0.5 (0-3.5) | 0.002* |
| V6p | 2 (0-4) | 1.5 (0-3.5) | 0.003* |

Values are presented as median and interquartile range.
*Significant Holm-Bonferroni adjusted p values.

The maximum 10-beat average QRSp (across the six precordial leads, V1 to V6) results for each patient group are shown in Table 2. Between the normal, ICM −VA and ICM +VA groups, there was a significant difference in V5p (0[0-0] vs. 2[0-4] vs. 6[4-7], p<0.001) and V6p (0[0-0.8] vs. 4[0-4] vs. 3[2-4.5], p=0.004). Subgroup analysis revealed V5p (i.e. QRSp score in precordial ECG lead V5) to be greater in ICM +VA patients than in normal (p<0.001) and ICM −VA (p=0.002) patients. V5p was the only QRSp value found to be greater in ICM −VA patients than in normal individuals (p=0.009). In contrast, QRSp derived from the 100-beat average was similar between the 3 groups for all precordial leads. Thus, it was seen in the study that the shorter 10-beat average window was more predictive of heart disease and VA. There was no difference in RMS −ST noise levels between the groups.

To assess the clinical performance of the QRSp detection method, the specificity and sensitivity of V5p for identifying those at risk of VA amongst the 20 ICM patients was determined. A V5p threshold of 3 was found to achieve an optimal specificity of 70% and sensitivity of 90%.

TABLE 2

QRSp IN NORMAL, ICM −VA AND ICM +VA PATIENTS

| QRSp | Normal (N = 8) | ICM −VA (N = 10) | ICM +VA (N = 10) | P |
|---|---|---|---|---|
| V1p | 1 (0-2) | 2 (1.5-4) | 3 (2-6.8) | 0.08 |
| V2p | 1 (0-2) | 2 (0-4) | 2 (0-4) | 0.27 |
| V3p | 2 (0-4) | 0 (0-2.5) | 3 (1.5-4.5) | 0.21 |
| V4p | 0.5 (0-2) | 2 (1.5-4.5) | 2 (2-4.3) | 0.04 |
| V5p | 0 (0-0) | 2 (0-4) | 6 (4-7) | <0.001* |
| V6p | 0 (0-0.8) | 4 (0-4) | 3 (2-4.5) | 0.004* |

Values are presented as median and interquartile range.
*Significant Holm-Bonferroni adjusted p values.

Prospective Clinical Validation Study

An additional clinical study was conducted on patients with ischemic (ICM) or nonischemic (DCM) cardiomyopathy (n=99), who were undergoing prophylactic implantable cardioverter defibrillator (ICD) implantation with no prior history of ventricular arrhythmias. High resolution digital 12-lead-ECG Holters (CM 3000-12BT, Getemed, Germany) were used to record ECG data at a sampling rate of 1,024 Hz during intrinsic rhythm. ECG waveforms were downloaded for custom analysis of QRSp using an embodiment of the methods described herein. In summary, QRSp was quantified for each precordial lead (V1 to V6) based on the total number of abnormal deflections that deviated from its respective naive QRS template. QRSp was expressed for each precordial lead (Vnp), the maximum of all precordial leads (QRSp Max), and the mean of all precordial leads (QRSp Mean). In addition, other QRS metrics were evaluated including QRS duration (QRSd), QRS fractionation (fQRS; present or absent), Selvester QRS score, and QRS fractionation index (QRS FI). QRSd measures the duration of the QRS complex from its onset to offset [12]. fQRS is a qualitative metric that manually evaluates the presence or absence of QRS fractionation based on published criteria [13]. QRS FI is a quantitative metric that isolates the high frequency content of the QRS and computes the total number of extrema in the resulting high frequency signal [14].

Patients were followed prospectively every 6 months in the ambulatory ICD clinic to evaluate primary and secondary clinical endpoints. The primary endpoint of arrhythmic events was defined as appropriate ICD therapy or sustained ventricular tachyarrhythmias. The secondary endpoint of cardiac events that included the primary endpoint as well as cardiac death and heart transplantation.

Results

Main Study

QRSp was measurable with high signal to noise in each precordial lead (V1-V6) of all patients. There was no correlation (at a Bonferroni corrected significance level of p<0.008) between the RMS-ST noise level and the QRSp of each precordial lead (V1: $r=-0.03$, $p=0.72$; V2: $r=-0.03$, $p=0.75$; V3: $r=-0.26$, $p=0.01$; V4: $r=0.09$, $p=0.37$; V5:

r=−0.15, p=0.15; V6: r=−0.02, p=0.83). Thus, noise did not contribute to the low amplitude QRSp signal.

The baseline clinical characteristics of the patients are shown in Table 3. After a median follow-up of 24 (15-43) months, 20 patients had arrhythmic events and 25 patients had cardiac events. There was no difference in clinical characteristic between patients with arrhythmic events and those without arrhythmic events. There was also no difference in clinical characteristics between patients with cardiac events and those without cardiac events.

Figure 7A:
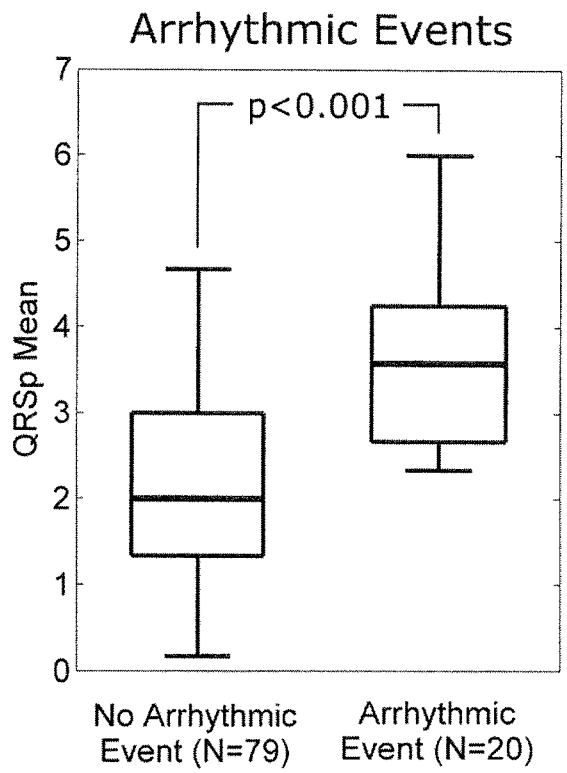
FIGS. 7A-7B show comparisons of QRSp Mean (i.e. mean QRS peak score) between arrhythmic and cardiac event groups in a clinical study.
Figure 7B:
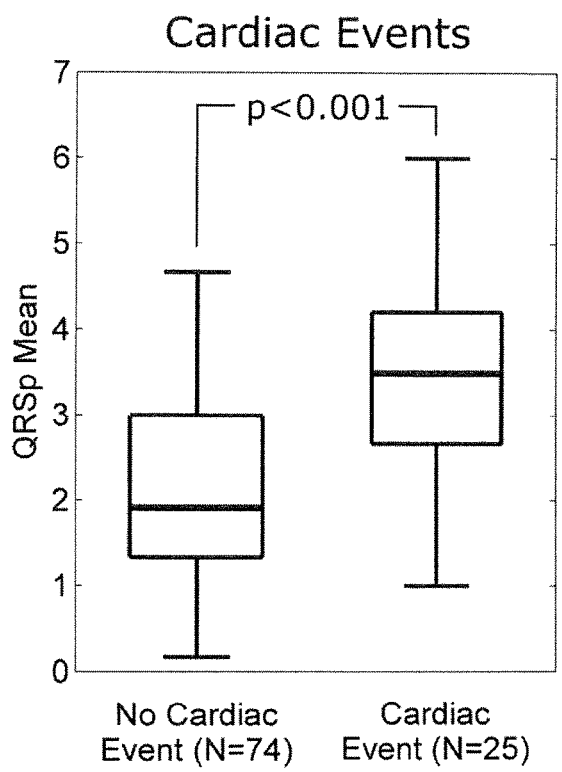
Figure 7C:
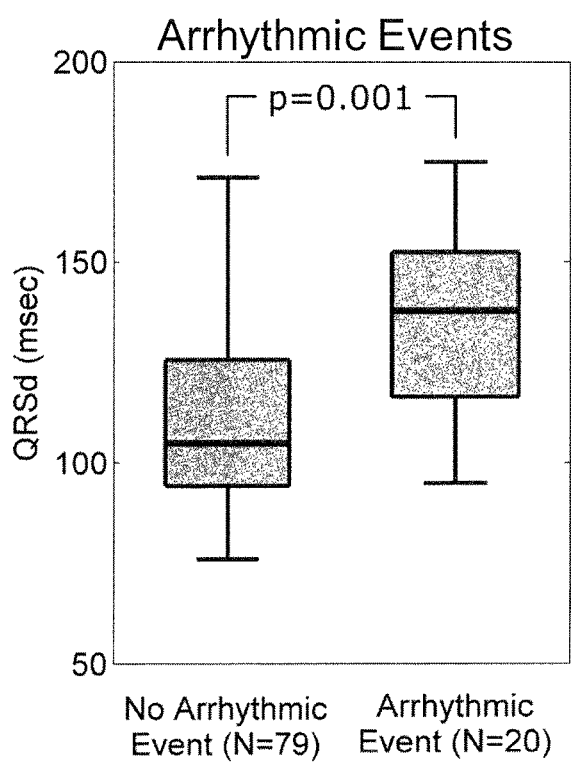
FIGS. 7C-7D show comparisons of QRSd (i.e. QRS duration) between arrhythmic and cardiac event groups in the clinical study.
Figure 7D:
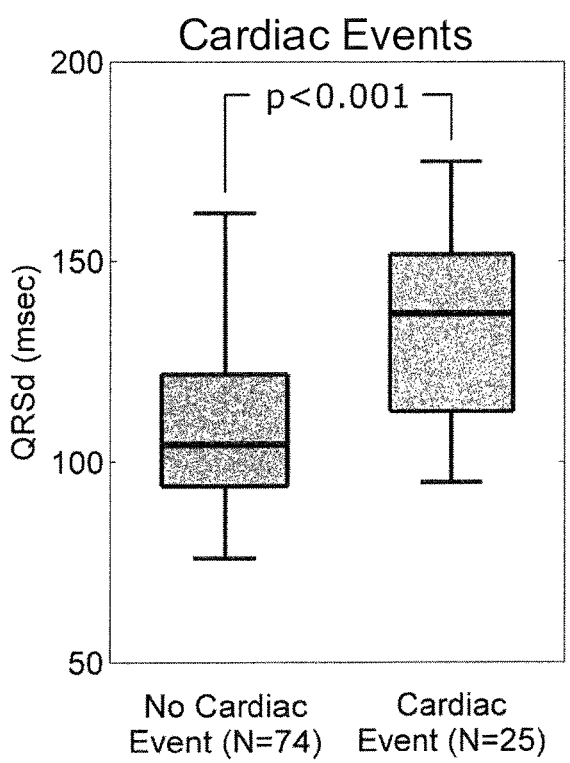

The ECG characteristics of the patients are shown in Table 4. Patients with arrhythmic/cardiac events had significantly greater QRSp (in individual precordial leads), QRSp Max, and QRSp Mean than those without arrhythmic/cardiac events (see FIGS. 7A-7B). Among the other QRS metrics, QRSd (see FIGS. 7C-7D) and QRS FI were both significantly greater in patients with arrhythmic/cardiac events than those without.

TABLE 3

| Patient characteristics | | | | | | | |
|---|---|---|---|---|---|---|---|
| | Total Popul'n (N = 99) | Arrhythmic Event Negative (N = 79) | Arrhythmic Event Positive (N = 20) | P | Cardiac Event Negative (N = 74) | Cardiac Event Positive (N = 25) | P |
| Follow-Up, mos | 24(15-43) | 24(16-50) | 19(10-34) | 0.07 | 24(16-52) | 22(11-34) | 0.18 |
| Age, yrs | 62 ± 11 | 61 ± 11 | 66 ± 7 | 0.12 | 62 ± 10 | 63 ± 11 | 0.59 |
| Male gender, n(%) | 84(85) | 68(86) | 16(80) | 0.50 | 63(85) | 21(84) | 1.00 |
| LVEF, % | 27 ± 7 | 27 ± 7 | 26 ± 7 | 0.68 | 27 ± 7 | 26 ± 7 | 0.53 |
| LVEF < 35%, n(%) | 84(85) | 67(85) | 17(85) | 1.00 | 62(84) | 22(88) | 0.75 |
| Primary Etiology of Cardiomyopathy | | | | | | | |
| Ischemic, n(%) | 61(62) | 48(61) | 13(65) | 0.80 | 46(62) | 15(60) | 1.00 |
| Non-ischemic dilated, n(%) | 38(38) | 31(39) | 7(35) | | 28(38) | 10(40) | |
| NYHA functional class, n(%) | | | | | | | |
| I | 33(33) | 24(30) | 9(45) | 0.43 | 23(31) | 10(40) | 0.19 |
| II | 44(44) | 35(44) | 9(45) | | 33(45) | 11(44) | |
| III | 21(21) | 19(24) | 2(10) | | 18(24) | 3(12) | |
| IV | 1(1) | 1(1) | 1(1) | | 0(0) | 1(4) | |
| Co-morbidities (n %) | | | | | | | |
| Hypertension | 51(52) | 41(52) | 10(50) | 1.00 | 39(53) | 12(48) | 0.82 |
| Diabetes | 44(44) | 33(42) | 11(55) | 0.32 | 30(41) | 14(56) | 0.25 |
| Hyperlipidemia | 60(61) | 44(56) | 16(80) | 0.07 | 42(57) | 18(72) | 0.24 |
| Smoking history | 48(49) | 39(49) | 9(45) | 0.81 | 37(50) | 11(44) | 0.65 |
| Prior revascularization | 50(51) | 37(47) | 13(65) | 0.21 | 35(47) | 15(60) | 0.36 |
| History of atrial fibrillation | 28(28) | 19(24) | 9(45) | 0.09 | 19(26) | 9(36) | 0.32 |
| Renal dysfunction* | 28(28) | 22(28) | 6(30) | 1.00 | 22(30) | 6(24) | 0.80 |
| Medications, (n %) | | | | | | | |
| Beta-blocker | 94(95) | 74(94) | 20(100) | 0.58 | 69(93) | 25(100) | 0.33 |
| ACE-I/ARB | 90(91) | 72(91) | 19(90) | 1.00 | 67(91) | 23(92) | 1.00 |
| Diuretic | 75(76) | 60(76) | 15(75) | 1.00 | 55(74) | 20(80) | 0.79 |
| Class III anti-arrhythmic | 11(11) | 7(9) | 4(20) | 0.23 | 7(10) | 4(16) | 0.46 |
| Calcium channel blockers | 4(4) | 4(5) | 0(0) | 0.58 | 4(5) | 0(0) | 0.57 |
| Lipid-lowering agents | 78(79) | 60(76) | 18(90) | 0.23 | 57(77) | 21(84) | 0.58 |
| Antiplatelet agents | 64(65) | 50(63) | 14(70) | 0.79 | 49(66) | 15(60) | 0.63 |

*eGFR < 61 mL/min/1.73 m$^2$

TABLE 4

ECG characteristics

| | Total Population (N = 99) | Arrhythmic Event Negative (N = 79) | Arrhythmic Event Positive (N = 20) | P | Cardiac Event Negative (N = 74) | Cardiac Event Positive (N = 25) | P |
|---|---|---|---|---|---|---|---|
| Baseline heart rate, bpm | 69 ± 12 | 68 ± 12 | 71 ± 13 | 0.37 | 68 ± 12 | 72 ± 12 | 0.12 |
| Repolarization Parameters | | | | | | | |
| QT Interv., ms | 428 ± 41 | 427 ± 41 | 430 ± 40 | 0.74 | 428 ± 42 | 427 ± 39 | 0.93 |
| QTc interv., ms | 452 ± 35 | 452 ± 36 | 451 ± 34 | 0.93 | 451 ± 36 | 454 ± 34 | 0.68 |
| Depolarization parameters | | | | | | | |
| QRSd, ms | 112(96-136) | 105(95-126) | 138(117-153) | 0.001 | 105(94-122) | 137(115-151) | <0.001 |
| QRSd ≥ 120 ms, n(%) | 43(43) | 29(37) | 14(70) | 0.01 | 26(35) | 17(68) | 0.005 |
| LBBB, n(%) | 19(19) | 12(15) | 7(35) | 0.06 | 10(14) | 9(36) | 0.020 |
| Presence of fQRS, n(%) | 68(69) | 53(67) | 15(75) | 0.60 | 51(69) | 17(68) | 1.00 |
| QRS Score | 6.0(3.0-9.0) | 7.0(2.0-9.0) | 6.0(3.0-9.0) | 0.95 | 6.0(2.0-9.0) | 7.0(3.0-9.0) | 0.37 |
| QRS Fractionation Index | | | | | | | |
| QRSp | 8.2(6.9-9.9) | 7.8(6.7-9.3) | 9.0(7.6-11.1) | 0.034 | 7.6(6.7-9.2) | 9(8.3-11.1) | 0.004 |
| V1p | 2.0(0.0-4.0) | 2.0(0.0-4.0) | 4.0(2.0-6.0) | <0.001* | 2.0(0.0-4.0) | 4.0(2.0-6.0) | <0.001* |
| V2p | 2.0(0.0-4.0) | 2.0(0.0-3.0) | 2.5(2.0-4.0) | 0.006* | 2.0(0.0-3.0) | 2.0(1.0-4.0) | 0.019 |
| V3p | 2.0(0.0-4.0) | 2.0(0.0-4.0) | 3.0(2.0-4.0) | 0.05 | 2.0(0.0-4.0) | 2.0(2.0-4.0) | 0.08 |
| V4p | 2.0(2.0-4.0) | 2.0(1.5-4.0) | 4.0(3.0-5.5) | <0.001* | 2.0(1.0-4.0) | 4.0(3.0-6.0) | <0.001* |
| V5p | 2.0(1.0-5.0) | 2.0(1.0-4.0) | 5.0(4.0-7.5) | <0.001* | 2.0(1.0-4.0) | 5.0(4.0-7.0) | <0.001* |
| V6p | 2.0(0.5-4.) | 2.0(0.0-4.0) | 4.0(3.0-6.0) | <0.001* | 2.0(0.0-4.0) | 4.0(2.0-5.0) | 0.001* |
| QRSp Max | 6.0(4.0-7.0) | 4.0(3.0-6.0) | 6.0(6.0-9.0) | 0.001* | 4.0(3.0-6.0) | 7.0(6.0-8.0) | <0.001* |
| QRSp Mean | 2.3(1.4-3.4) | 2.0(1.3-3.0) | 3.6(2.7-4.3) | <0.001* | 1.9(1.3-3.0) | 3.5(2.7-4.2) | <0.001* |

*QRSp variables below Bonferroni corrected significance level (p < 0.00625)

Cox regression analysis was used to assess the predictive value of QRSp Mean for arrhythmic/cardiac events (Table 5). Previously established clinical predictors (age and left ventricular ejection fraction (LVEF)) and the QRS metrics that were significant univariable predictors (QRS FI and QRSp Mean, p<0.1) were used to construct two separate multivariable models. Because of co-linearity between QRSp Mean and QRS FI, these two variables were evaluated separately in the models as follows: In Model #1 that included age, LVEF, QRSd and QRS FI, only QRSd was an independent predictor of arrhythmic/cardiac events. In Model #2 that included age, LVEF, QRSd and QRSp Mean, only QRSp Mean was an independent predictor of arrhythmic/cardiac events. Thus, QRS FI was not an independent predictor of arrhythmic/cardiac events in either multivariable model, while QRSd and QRSp Mean were the only independent predictor of arrhythmic/cardiac events in Model #1 and Model #2, respectively.

TABLE 5

Cox regression analysis for prediction of arrhythmic and cardiac events

| | Univariable Analysis | | Multivariable Model #1 | | Multivariable Model #2 | |
|---|---|---|---|---|---|---|
| | HR (95% CI) | P | HR (95% CI) | P | HR (95% CI) | P |
| | Arrhythmic Events | | | | | |
| Age (per 5 yrs) | 1.19 (0.94-1.50) | 0.15 | 1.14 (0.88-1.47) | 0.33 | 1.20 (0.93-1.55) | 0.17 |
| LVEF (per 5%) | 0.91 (0.66-1.26) | 0.57 | 0.99 (0.71-1.39) | 0.96 | 1.01 (0.68-1.51) | 0.95 |
| QRSd (per 10 ms) | 1.27 (1.09-1.47) | 0.002 | 1.50 (1.13-2.01) | 0.006 | 1.11 (0.92-1.33) | 0.28 |
| Presence of fQRS | 1.38 (0.50-3.81) | 0.53 | — | — | — | — |
| QRS Score | 1.02 (0.93-1.12) | 0.68 | — | — | — | — |
| QRS Fractionation Index | 1.19 (0.99-1.44) | 0.070 | 0.78 (0.55-1.12) | 0.18 | — | — |
| Mean QRSp | 2.13 (1.56-2.92) | <0.001 | — | — | 1.96 (1.39-2.78) | <0.001 |
| | Cardiac Events | | | | | |
| Age (per 5 yrs) | 1.06 (0.88-1.28) | 0.560 | 1.02 (0.82-1.26) | 0.87 | 1.06 (0.86-1.29) | 0.58 |
| LVEF (per 5%) | 0.91 (0.68-1.21) | 0.510 | 1.00 (0.74-1.35) | 1.00 | 1.01 (0.71-1.45) | 0.94 |
| QRSd (per 10 ms) | 1.28 (1.11-1.46) | <0.001 | 1.46 (1.11-1.91) | 0.006 | 1.13 (0.96-1.33) | 0.13 |

TABLE 5-continued

Cox regression analysis for prediction of arrhythmic and cardiac events

|  | Univariable Analysis | | Multivariable Model #1 | | Multivariable Model #2 | |
|---|---|---|---|---|---|---|
|  | HR (95% CI) | P | HR (95% CI) | P | HR (95% CI) | P |
| Presence of fQRS | 0.95 (0.41-2.2) | 0.900 | — | — | — | — |
| QRS Score | 1.06 (0.98-1.15) | 0.180 | — | — | — | — |
| QRS Fractionation Index | 1.23 (1.04-1.46) | 0.010 | 0.83 (0.60-1.15) | 0.26 | — | — |
| Mean QRSp | 2.09 (1.56-2.79) | <0.001 | — | — | 1.89 (1.38-2.59) | <0.001 |

Based on the results of the multivariable models above, ROC curve analysis was used to evaluate the performance characteristics of QRSp Mean compared to QRSd. The area under the ROC curve trended to be greater (p=0.11) for QRSp Mean than QRSd. Using a QRSp Mean cutpoint of ≥2.25, the sensitivity and negative predictive value for identifying arrhythmic events were 100% and 100%, respectively (see FIG. 8A). With the same cutpoint, the sensitivity and negative predictive value of QRSp Mean for identifying cardiac events were 96% and 98%, respectively (see FIG. 8B). In comparison, the sensitivity and negative predictive value for QRSd≥120 ms (traditional cut-point used in clinical practice) was significantly lower for both arrhythmic (p<0.05) and cardiac events (p<0.05), while there was no difference in specificity and positive predictive value (see FIGS. 8A-8B).

Figure 9:
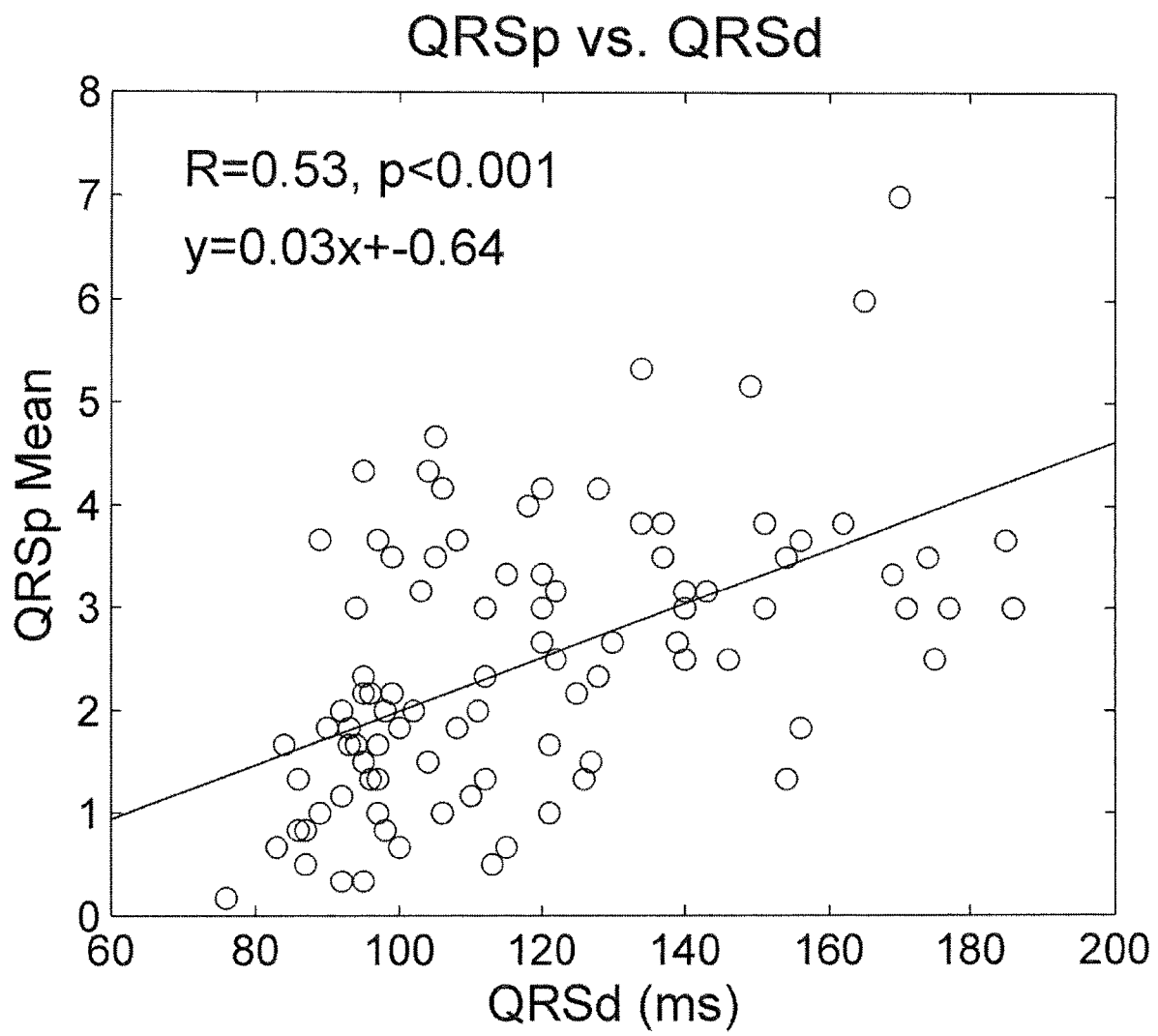
FIG. 9 shows the correlation of QRSp Mean and QRSd in the clinical study.
Figure 10:
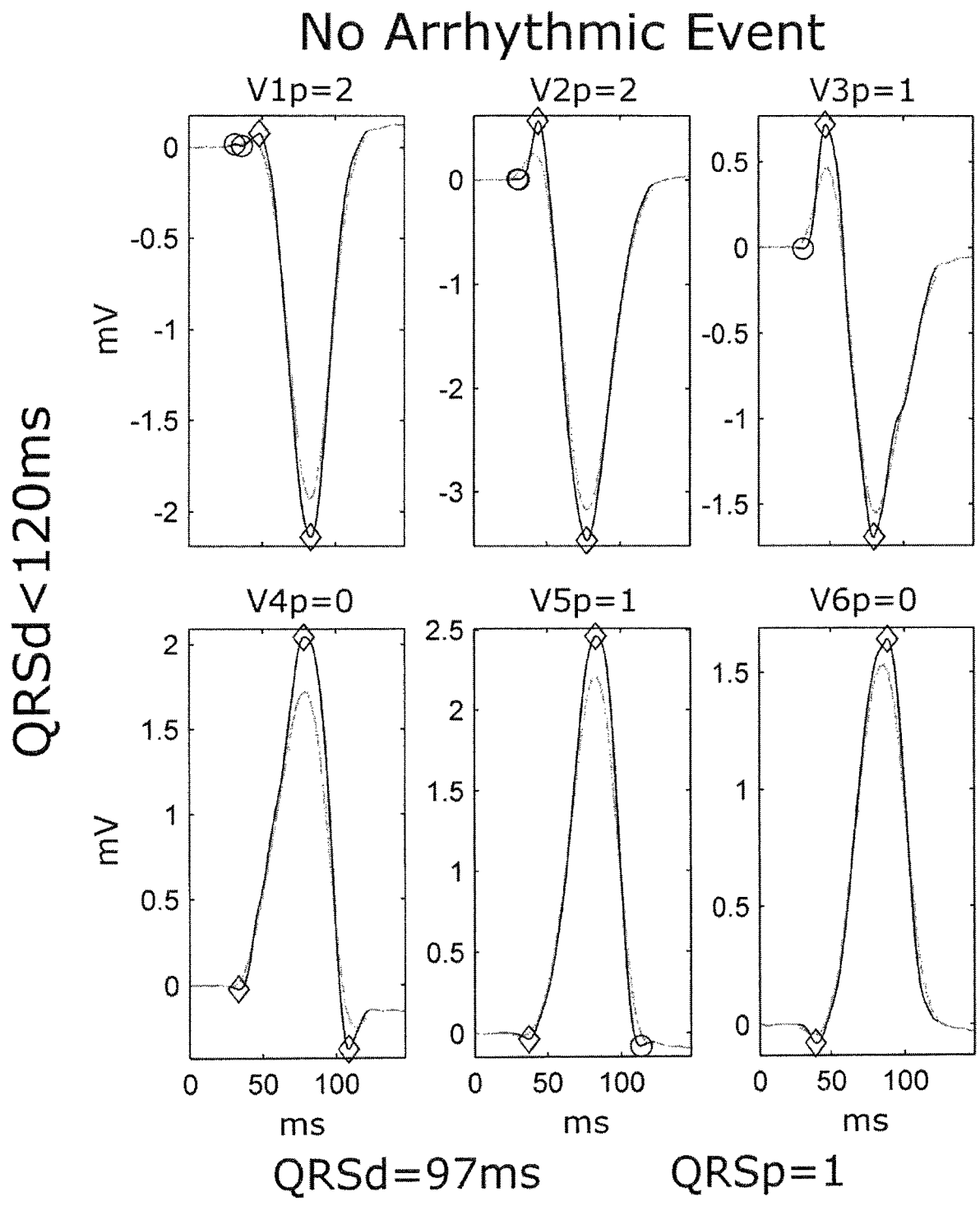
FIG. 10 is an illustration of QRSp Mean in a patient with narrow QRS duration without an arrhythmic event in the clinical study.
Figure 11:
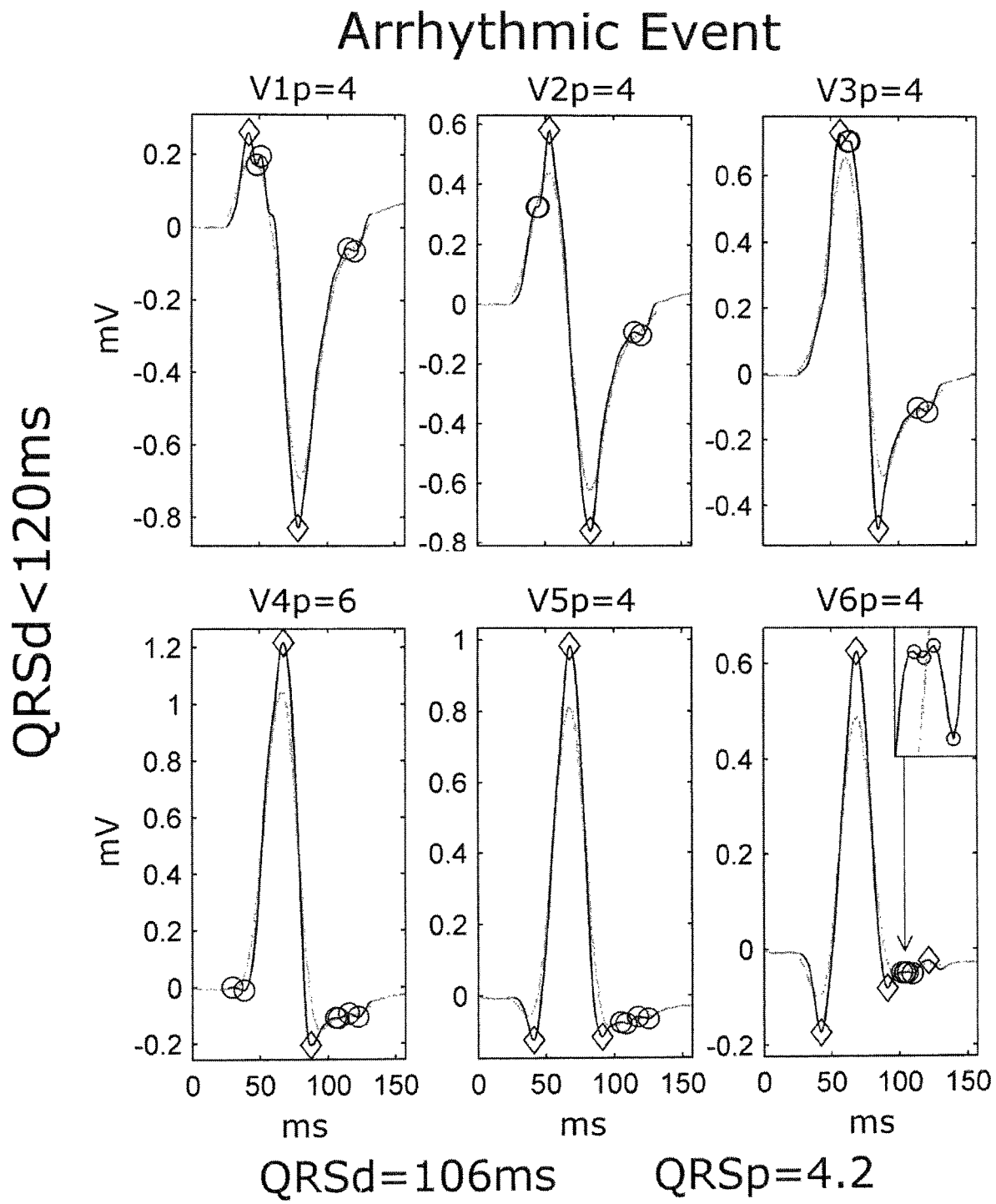
FIG. 11 is an illustration of QRSp Mean in a patient with narrow QRS duration with an arrhythmic event in the clinical study.
Figure 12:
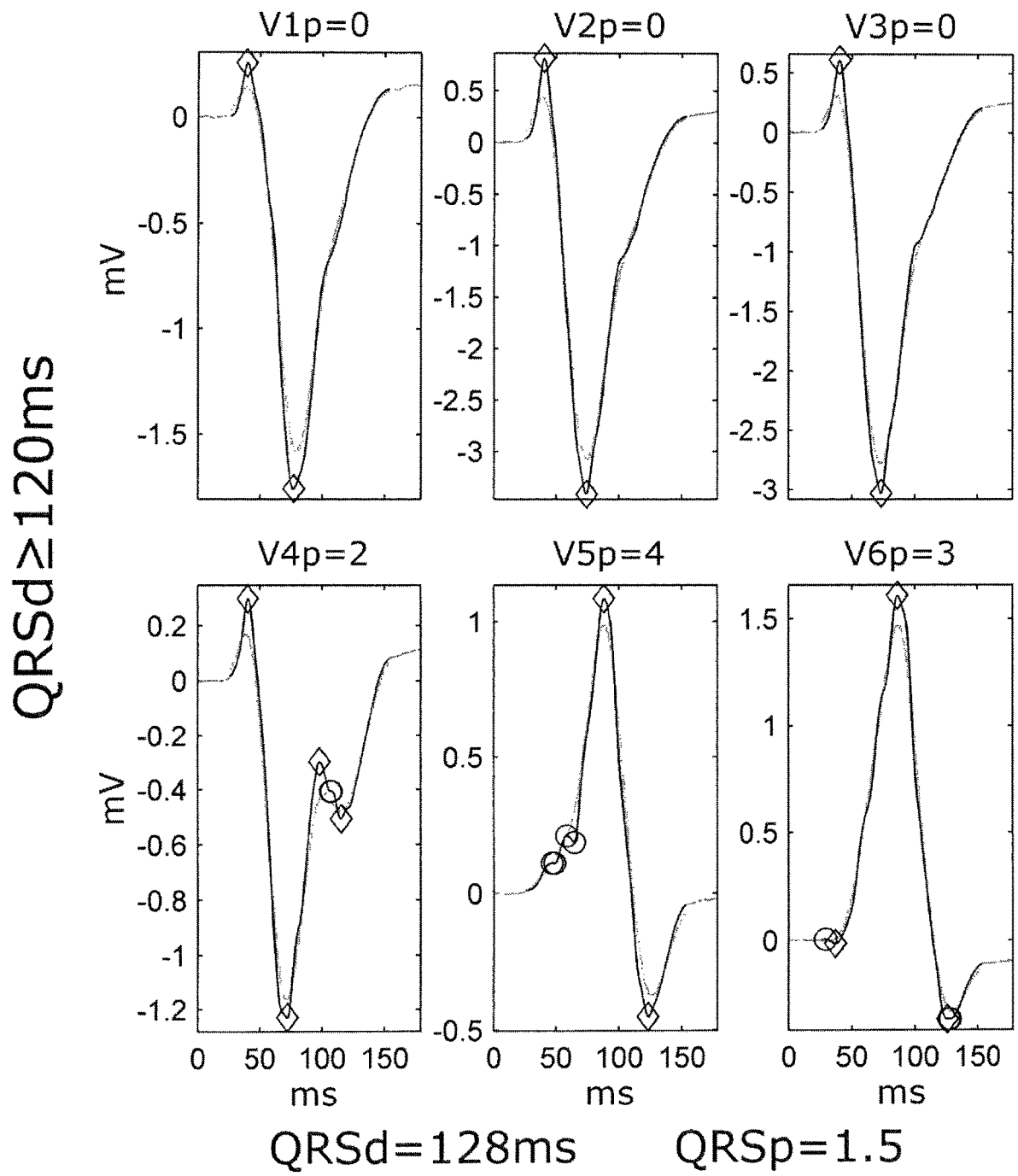
FIG. 12 is an illustration of QRSp Mean in a patient with broad QRS duration without an arrhythmic event in the clinical study.
Figure 13:
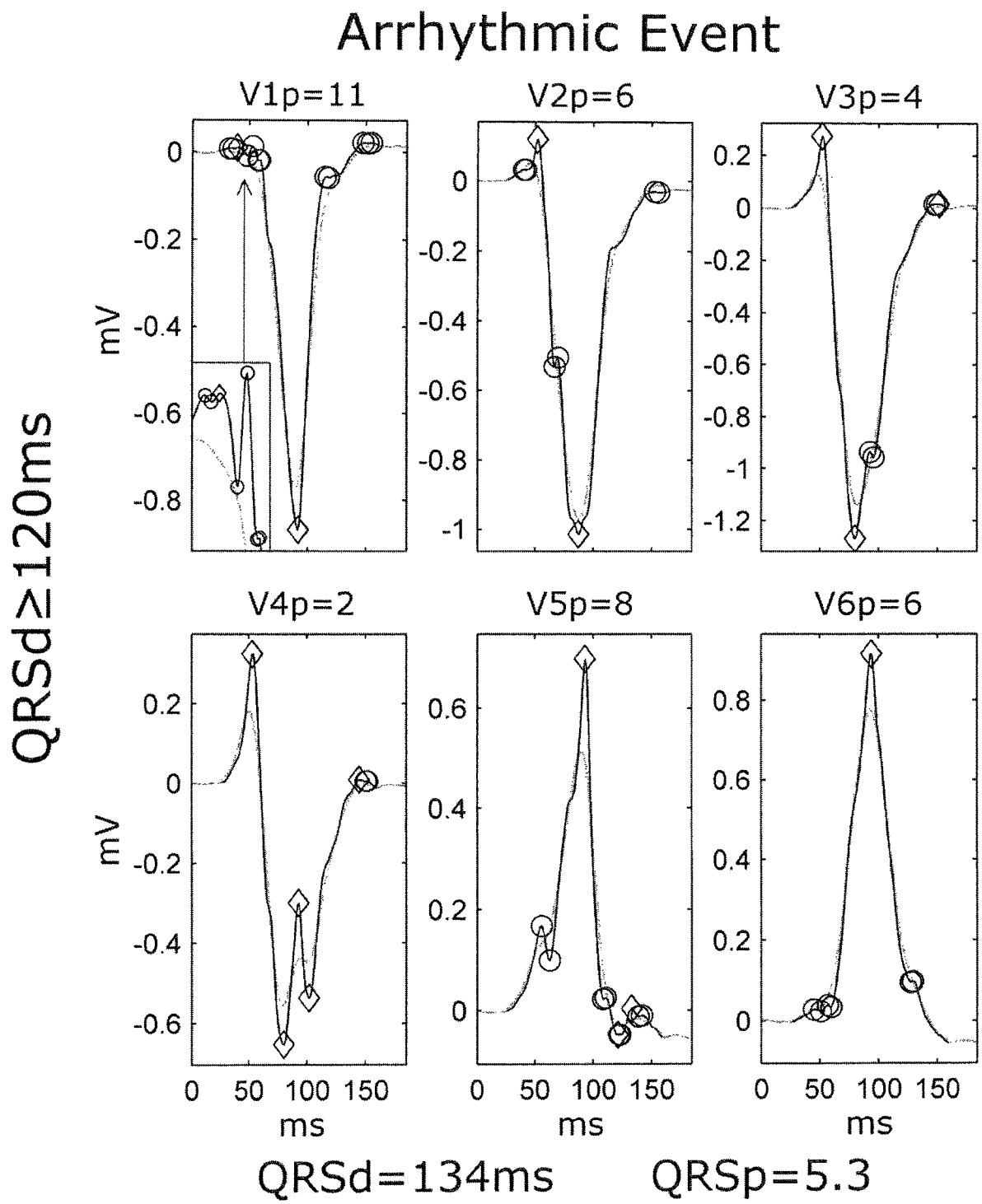
FIG. 13 is an illustration of QRSp Mean in a patient with broad QRS duration with an arrhythmic event in the clinical study.

The QRSp Mean did not strongly correlate with QRSd (see FIG. 9). FIGS. 10 and 11 illustrate 2 patients with QRSd<120 ms who have either small or large QRSp Mean, respectively. FIGS. 12 and 13 illustrate 2 patients with QRS 2120 ms who have either small or large QRSp Mean, respectively. The dark line indicates the short windowed QRS average (i.e. local QRS complex), while the light gray line indicates the long windowed QRS average (i.e. global QRS complex) for each ECG lead. The diamond indicates normal QRSp and the circle indicates abnormal positive/negative QRSp for each ECG lead.

The clinical and ECG characteristics of patients with QRSp Mean<2.25 versus QRSp Mean≥2.25 are presented in Table 6 and Table 7, respectively. No differences in clinical characteristics were observed. Patients with QRSp Mean≥2.25 had significantly greater QTc interval, QRSd, QRS Score, QRS FI and QRSp Mean. The proportion of patients with QRSd≥120 ms and LBBB was also significantly greater amongst those with QRSp Mean≥2.25.

Subanalysis was performed for the ICM (n=61) and DCM (n=38) groups. A comparison of the clinical characteristics between these groups is presented in Table 8. ICM patients were significantly older than DCM patients. A comparison of the ECG characteristics between these groups is presented in Table 9. ICM patients had significantly larger QRSp Mean and QRS score than DCM patients.

TABLE 6

QRSp Mean <2.25 vs. QRSp Mean ≥2.25 Patient Characteristics

|  | Total Population (N = 99) | QRSp <2.25 Population (N = 47) | QRSp ≥2.25 Population (N = 52) | P |
|---|---|---|---|---|
| Follow-Up, mos | 24(15-43) | 24(14-50) | 24(15-39) | 0.45 |
| Age, yrs | 62 ± 11 | 60 ± 11 | 64 ± 10 | 0.19 |
| Male gender, n (%) | 84(85) | 38(81) | 46(89) | 0.40 |
| LVEF, % | 27 ± 7 | 28 ± 7 | 26 ± 6 | 0.21 |
| LVEF <35%, n (%) | 84(85) | 38(81) | 46(89) | 0.40 |
| Primary Etiology of Cardiomyopathy | | | | |
| Ischemic, n (%) | 61(62) | 25(53) | 36(69) | 0.15 |
| Non-ischemic dilated, n (%) | 38(38) | 22(47) | 16(31) | |
| NYHA functional class, n (%) | | | | |
| I | 33(33) | 13(27) | 20(39) | 0.32 |
| II | 44(44) | 21(45) | 23(44) | |
| III | 21(21) | 13(28) | 8(15) | |
| IV | 1(1) | 0(0) | 1(2) | |
| Co-morbidities | | | | |
| Hypertension, n (%) | 51(52) | 25(53) | 26(50) | 0.84 |
| Diabetes, n (%) | 44(44) | 20(43) | 24(46) | 0.84 |
| Hyperlipidemia, n (%) | 60(61) | 26(55) | 34(65) | 0.41 |
| Smoking history, n (%) | 48(49) | 26(55) | 22(42) | 0.23 |
| Prior revascularization, n (%) | 50(51) | 22(47) | 28(54) | 0.55 |
| History of atrial fibrillation, n (%) | 28(28) | 10(21) | 18(35) | 0.18 |
| Renal dysfunction*, n (%) | 28(28) | 15(32) | 13(25) | 0.51 |
| Medications | | | | |
| Beta-blocker, n (%) | 94(95) | 45(96) | 49(94) | 1.00 |
| ACE-I/ARB, n (%) | 90(91) | 41(87) | 49(94) | 0.30 |
| Diuretic, n (%) | 75(76) | 35(75) | 40(77) | 0.82 |

TABLE 6-continued

QRSp Mean <2.25 vs. QRSp Mean ≥2.25 Patient Characteristics

| | Total Population (N = 99) | QRSp <2.25 Population (N = 47) | QRSp ≥2.25 Population (N = 52) | P |
|---|---|---|---|---|
| Class III anti-arrhythmic, n (%) | 11(11) | 4(9) | 7(14) | 0.53 |
| Calcium channel blockers, n (%) | 4(4) | 2(4) | 2(4) | 1.00 |
| Lipid-lowering agents, n (%) | 78(79) | 36(77) | 42(81) | 0.63 |
| Antiplatelet agents, n (%) | 64(65) | 29(62) | 35(67) | 0.67 |

TABLE 7

QRSp Mean <2.25 vs. QRSp Mean ≥2.25 ECG Characteristics

| | Total Population (N = 99) | QRSp <2.25 Population (N = 47) | QRSp ≥2.25 Population (N = 52) | P |
|---|---|---|---|---|
| Baseline heart rate, bpm | 69 ± 12 | 69 ± 12 | 69 ± 12 | 0.93 |
| Repolarization Parameters | | | | |
| QT Interval, ms | 428 ± 41 | 420 ± 39 | 435 ± 42 | 0.07 |
| QTc interval, ms | 452 ± 35 | 444 ± 32 | 459 ± 37 | 0.033 |
| Depolarization parameters | | | | |
| QRSd, ms | 112(96-136) | 97(92-109) | 129(112-151) | <0.001 |
| QRSd ≥120 ms, n (%) | 43(43) | 7(15) | 36(69) | <0.001 |
| LBBB, n (%) | 19(19) | 3(6) | 16(31) | 0.002 |
| Presence of fQRS, n (%) | 68(69) | 33(70) | 35(67) | 0.83 |
| QRS Score | 6.0(3.0-9.0) | 4.0(1.5-8.0) | 8.0(5.5-10.0) | <0.001 |
| QRS Fractionation Index | 8.2(6.9-9.9) | 6.9(6.0-7.9) | 9.2(8.2-11.3) | <0.001 |
| QRSp Mean | 2.3(1.4-3.5) | 1.3(0.9-1.8) | 3.3(3.0-3.8) | <0.001 |

TABLE 8

ICM vs. DCM Patient Characteristics

| | Total Population (N = 99) | ICM Population (N = 61) | DCM Population (N = 38) | P |
|---|---|---|---|---|
| Follow-Up, mos | 24(15-43) | 24(16-39) | 19(13-43) | 0.49 |
| Age, yrs | 62 ± 11 | 64 ± 8 | 59 ± 13 | 0.021 |
| Male gender, n (%) | 84(85) | 55(90) | 29(76) | 0.08 |
| LVEF, % | 27 ± 7 | 28 ± 6 | 25 ± 7 | 0.06 |
| LVEF <35%, n (%) | 84(85) | 50(82) | 34(90) | 0.40 |
| NYHA functional class, n (%) | | | | |
| I | 33(33) | 19(31) | 14(37) | 0.55 |
| II | 44(44) | 28(46) | 16(42) | |
| III | 21(21) | 14(23) | 7(18) | |
| IV | 1(1) | 0(0) | 1(3) | |
| Co-morbidities | | | | |
| Hypertension, n (%) | 51(52) | 34(56) | 17(45) | 0.31 |
| Diabetes, n (%) | 44(44) | 27(44) | 17(45) | 1.00 |
| Hyperlipidemia, n (%) | 60(61) | 41(67) | 19(50) | 0.10 |
| Smoking history, n (%) | 48(49) | 27(44) | 21(55) | 0.31 |
| Prior revascularization, n (%) | 50(51) | 48(79) | 2(5) | <0.001 |
| History of atrial fibrillation, n (%) | 28(28) | 16(26) | 12(32) | 0.65 |
| Renal dysfunction*, n (%) | 28(28) | 19(31) | 9(24) | 0.50 |
| Medications | | | | |
| Beta-blocker, n (%) | 94(95) | 56(92) | 38(100) | 0.15 |
| ACE-I/ARB, n (%) | 90(91) | 54(89) | 36(95) | 0.48 |
| Diuretic, n (%) | 75(76) | 42(69) | 33(87) | 0.05 |
| Class III anti-arrhythmic, n (%) | 11(11) | 8(13) | 3(8) | 0.52 |
| Calcium channel blockers, n (%) | 4(4) | 3(5) | 1(3) | 1.00 |
| Lipid-lowering agents, n (%) | 78(79) | 56(92) | 22(58) | <0.001 |
| Antiplatelet agents, n (%) | 64(65) | 50(82) | 14(37) | <0.001 |

TABLE 9

| | Total Population (N = 99) | ICM Population (N = 61) | DCM Population (N = 38) | P |
|---|---|---|---|---|
| ICM vs. DCM ECG Characteristics | | | | |
| Baseline heart rate, bpm | 69 ± 12 | 67 ± 10 | 72 ± 14 | 0.027 |
| Repolarization Parameters | | | | |
| QT Interval, ms | 428 ± 41 | 432 ± 34 | 421 ± 50 | 0.25 |
| QTc interval, ms | 452 ± 35 | 451 ± 35 | 453 ± 35 | 0.78 |
| Depolarization parameters | | | | |
| QRSd, ms | 112(96-136) | 111(96-139) | 114(95-128) | 0.71 |
| QRSd ≥120 ms, n (%) | 43(43) | 26(43) | 17(45) | 0.84 |
| LBBB, n (%) | 19(19) | 9(15) | 10(26) | 0.19 |
| Presence of fQRS, n (%) | 68(69) | 42(69) | 26(68) | 1.00 |
| QRS Score | 6.0(3.0-9.0) | 8.0(6.0-11.0) | 3.0(2.0-6.0) | <0.001 |
| QRS Fractionation Index | 8.2(6.9-9.9) | 8.2(7.2-10.2) | 7.8(5.8-9.0) | 0.10 |
| QRSp Mean | 2.3(1.4-3.5) | 2.7(1.7-3.7) | 1.8(1.0-3.0) | 0.007 |

Ischemic Cardiomyopathy Subgroup Analysis

Figure 14A:
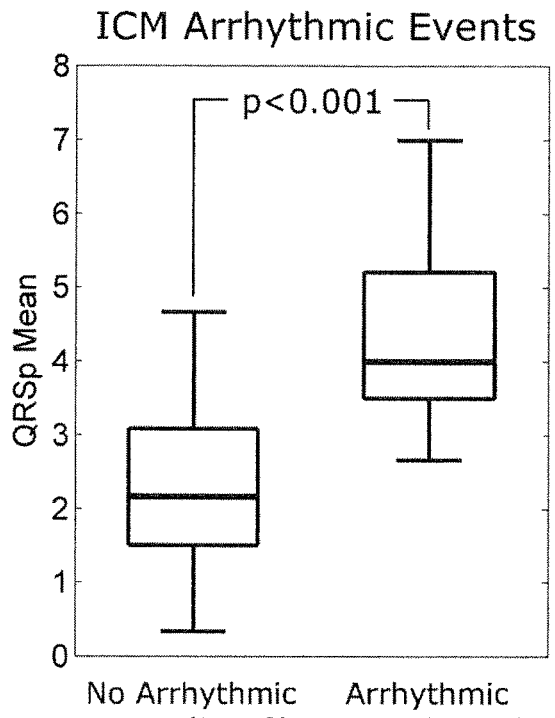
FIGS. 14A-14B show comparisons of QRSp Mean between arrhythmic and cardiac event groups in patients with ICM (i.e. Ischemic CardioMyopathy) in the clinical study.
Figure 14B:
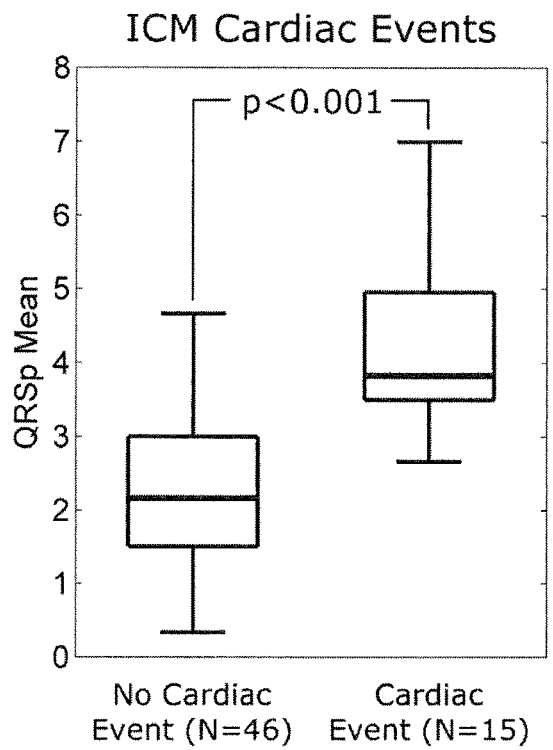
Figure 14C:
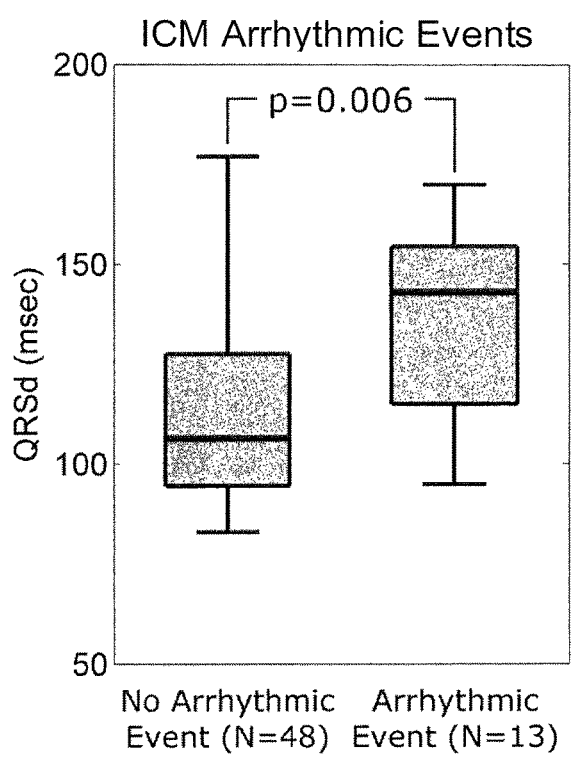
FIGS. 14C-14D show comparisons of QRSd between arrhythmic and cardiac event groups in patients with ICM in the clinical study.
Figure 14D:
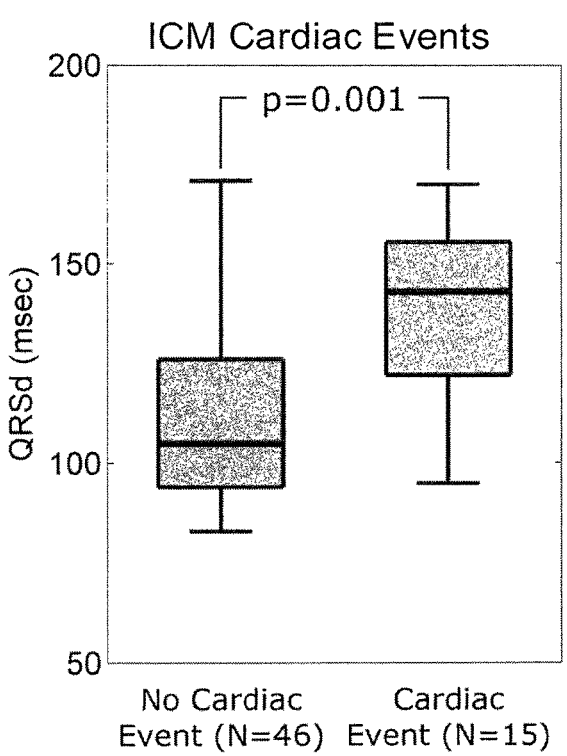

The clinical and ECG characteristics of the ICM group are presented in Table 10 and Table 11, respectively. ICM patients with arrhythmic/cardiac events had significantly less revascularization and more atrial fibrillation than those without these events. ICM patients with arrhythmic/cardiac events had significantly greater QRSp Mean than those without arrhythmic/cardiac events (see FIGS. 14A-14B). Among the other QRS metrics, QRSd and QRS FI were significantly greater in patients with arrhythmic/cardiac events than those without (see FIGS. 14C-14D). The proportion of patients with QRSd≥120 ms and LBBB was also significantly greater amongst those with cardiac events.

In ICM patients, ROC analysis was used to evaluate the performance characteristics of QRSp Mean compared to QRSd. The area under the ROC curve trended to be greater (p>0.05) for QRSp Mean than QRSd. Using a QRSp Mean cutpoint of ≥2.58, the sensitivity and negative predictive value for identifying arrhythmic events were 100% and 100%, respectively (see FIG. 15A). With the same cutpoint, the sensitivity and negative predictive value of QRSp Mean in identifying cardiac events were 100% and 100%, respectively (see FIG. 15B). In comparison, the sensitivity and negative predictive value for QRSd≥120 ms was lower for both arrhythmic and cardiac events, while there was no difference in specificity and positive predictive value (see FIGS. 15A-15B).

TABLE 10

| | ICM Popul'n (N = 61) | Arrhythmic Event Negative (N = 48) | Arrhythmic Event Positive (N = 13) | P | Cardiac Event Negative (N = 46) | Cardiac Event Positive (N = 15) | P |
|---|---|---|---|---|---|---|---|
| ICM Patient Characteristics | | | | | | | |
| Follow-Up, mos | 24(16-39) | 25(19-54) | 18(8-30) | 0.07 | 24(19-56) | 22(11-29) | 0.12 |
| Age, yrs | 64 ± 8 | 64 ± 9 | 65 ± 5 | 0.66 | 64 ± 9 | 66 ± 5 | 0.52 |
| Male gender, n(%) | 55(90) | 43(90) | 12(92) | 1.00 | 41(89) | 14(93) | 1.00 |
| LVEF, % | 28 ± 6 | 28 ± 6 | 29 ± 6 | 0.70 | 28 ± 6 | 28 ± 6 | 0.90 |
| LVEF < 35%, n(%) | 50(82) | 39(81) | 11(85) | 1.00 | 37(80) | 13(87) | 0.72 |
| NYHA functional class, n(%) | | | | | | | |
| I | 19(31) | 14(29) | 5(39) | 0.34 | 14(30) | 5(33) | 0.20 |
| II | 28(46) | 21(44) | 7(54) | | 19(41) | 9(60) | |
| III | 14(23) | 13(27) | 1(8) | | 13(28) | 1(7) | |
| IV | 0(0) | 0(0) | 0(0) | | 0(0) | 0(0) | |
| Co-morbidities | | | | | | | |
| Hypertension, n(%) | 34(56) | 26(54) | 8(62) | 0.76 | 25(54) | 9(60) | 0.77 |
| Diabetes, n(%) | 27(44) | 21(44) | 6(46) | 1.00 | 19(41) | 8(53) | 0.55 |
| Hyperlipidemia, n(%) | 41(67) | 31(65) | 10(77) | 0.52 | 31(67) | 10(67) | 1.00 |
| Smoking history, n(%) | 27(44) | 23(48) | 4(31) | 0.35 | 22(48) | 5(33) | 0.38 |
| Prior revascularization, n(%) | 48(79) | 35(73) | 13(100) | 0.05 | 33(71) | 15(100) | 0.026 |
| History of atrial fibrillation, n(%) | 16(26) | 9(19) | 7(54) | 0.028 | 9(20) | 7(47) | 0.05 |
| Renal dysfunction*, n(%) | 19(31) | 15(31) | 4(31) | 1.00 | 15(33) | 4(27) | 0.76 |
| Medications | | | | | | | |
| Beta-blocker, n(%) | 56(92) | 43(90) | 13(100) | 0.58 | 41(89) | 15(100) | 0.32 |
| ACE-I/ARB, n(%) | 54(89) | 43(90) | 11(85) | 0.63 | 41(89) | 13(87) | 1.00 |
| Diuretic, n(%) | 42(69) | 33(69) | 9(69) | 1.00 | 31(67) | 11(73) | 0.76 |
| Class III anti-arrhythmic, n(%) | 8(13) | 5(10) | 3(23) | 0.35 | 5(11) | 3(20) | 0.39 |
| Calcium channel blockers, n(%) | 3(5) | 3(6) | 0(0) | 1.00 | 3(7) | 0(0) | 0.57 |
| Lipid-lowering agents, n(%) | 56(92) | 44(92) | 12(92) | 1.00 | 43(94) | 13(87) | 0.59 |
| Antiplatelet agents, n(%) | 50(82) | 40(83) | 10(77) | 0.69 | 39(85) | 11(73) | 0.44 |

*eGFR < 61 mL/min/1.73 m$^2$

TABLE 11

ICM ECG Characteristics

|  | ICM Population (N = 61) | Arrhythmic Event Negative (N = 48) | Arrhythmic Event Positive (N = 13) | P | Cardiac Event Negative (N = 46) | Cardiac Event Positive (N = 15) | P |
|---|---|---|---|---|---|---|---|
| Baseline heart rate, bpm | 67 ± 10 | 66 ± 10 | 69 ± 9 | 0.31 | 65 ± 10 | 70 ± 9 | 0.13 |
| Repolarization Par. | | | | | | | |
| QT Interval, ms | 432 ± 34 | 432 ± 35 | 429 ± 30 | 0.75 | 432 ± 35 | 430 ± 30 | 0.84 |
| QTc interval, ms | 451 ± 35 | 451 ± 37 | 451 ± 30 | 0.99 | 449 ± 36 | 455 ± 33 | 0.58 |
| Depolarization Par. | | | | | | | |
| QRSd, ms | 111(96-139) | 107(95-128) | 143(118-154) | 0.006 | 105(94-126) | 143(126-155) | 0.001 |
| QRSd ≥ 120 ms, n(%) | 26(43) | 17(35) | 9(69) | 0.06 | 15(33) | 11(73) | 0.008 |
| LBBB, n(%) | 9(15) | 5(10) | 4(31) | 0.09 | 3(7) | 6(40) | 0.005 |
| Presence of fQRS n(%) | 42(69) | 32(67) | 10(77) | 0.74 | 32(70) | 10(68) | 1.00 |
| QRS Score | 8.0(6.0-11.0) | 8.0(5.0-11.5) | 8.0(6.0-9.0) | 0.99 | 8.0(5.0-11.0) | 8.0(6.5-13.0) | 0.36 |
| QRS Fractionation Ind. | 8.2(7.2-10.2) | 7.9(6.9-9.7) | 10.4(8.3-11.2) | 0.023 | 7.8(6.9-9.5) | 10.4(8.3-11.3) | 0.007 |
| QRSp Mean | 2.7(1.7-3.7) | 2.2(1.5-3.1) | 4(3.5-5.2) | <0.001 | 2.2(1.5-3.0) | 3.8(3.5-4.8) | <0.001 |

Dilated Cardiomyopathy Subgroup Analysis

Figure 16A:
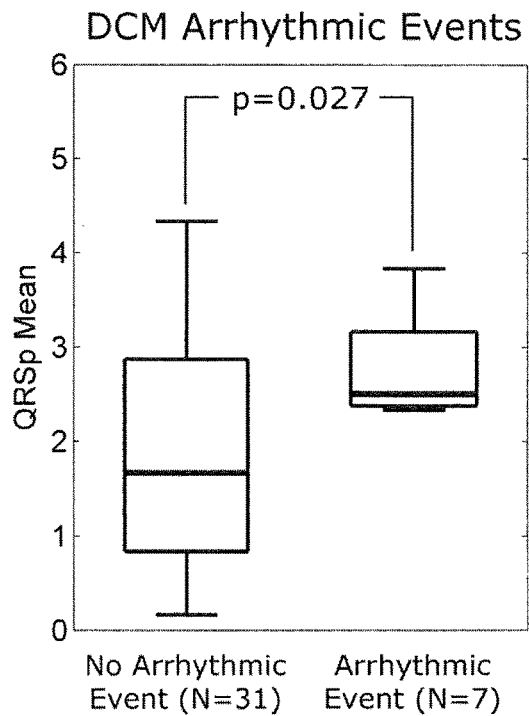
FIGS. 16A-16B show comparisons of QRSp Mean between arrhythmic and cardiac event groups in patients with DCM (i.e. non-ischemic Dilated CardioMyopathy) in the clinical study.
Figure 16B:
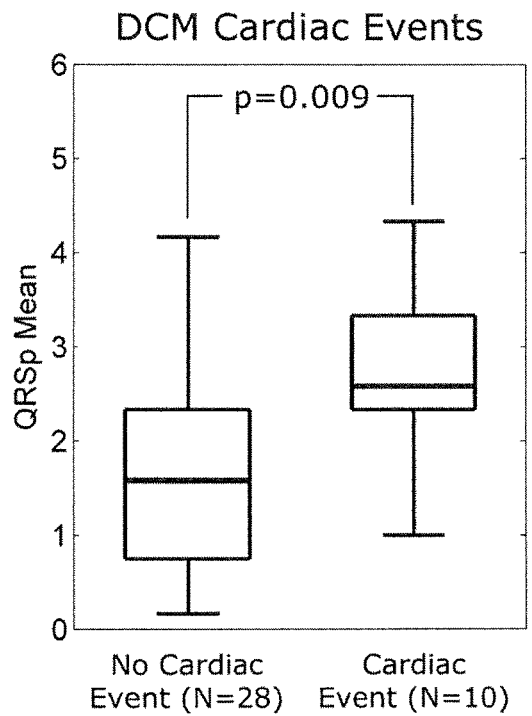
Figure 16C:
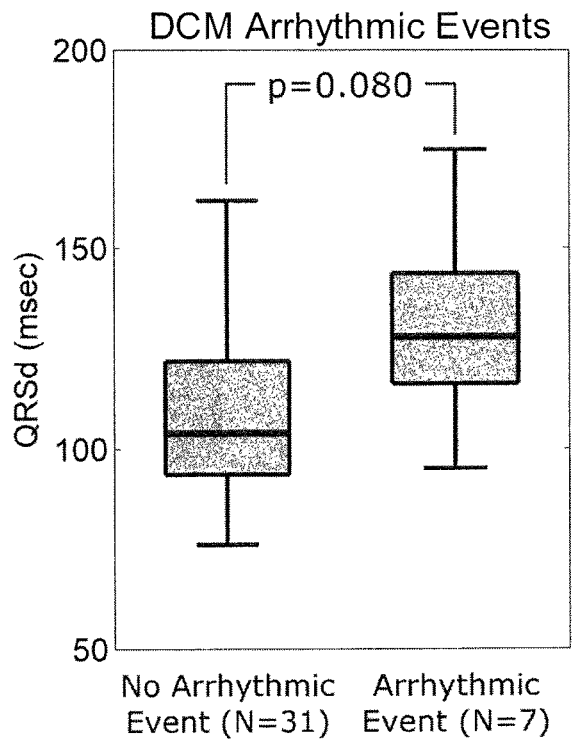
FIGS. 16C-16D show comparisons of QRSd between arrhythmic and cardiac event groups in patients with DCM in the clinical study.
Figure 16D:
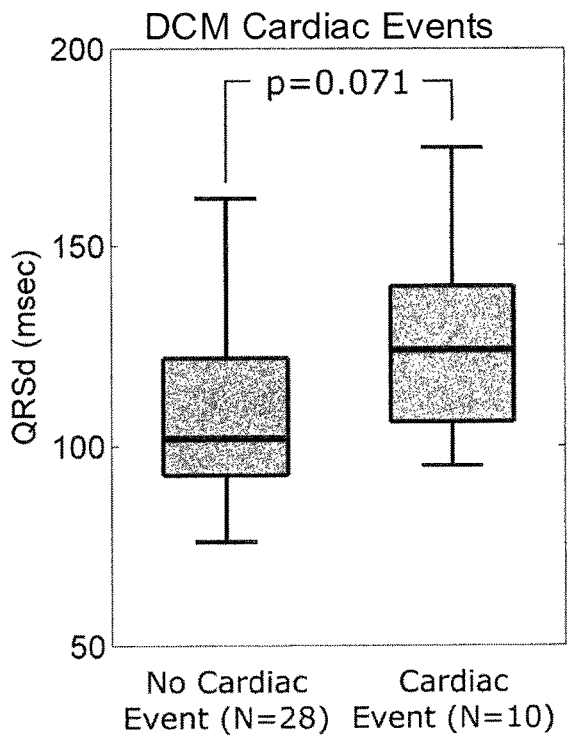

The clinical and ECG characteristics of the DCM group are presented in Table 12 and Table 13, respectively. The clinical characteristics of DCM patients with arrhythmic/cardiac events were similar to those without these events. DCM patients with arrhythmic/cardiac events had significantly greater QRSp Mean than those without arrhythmic/cardiac events (see FIGS. 16A-16B). Among the other QRS metrics, none were significantly greater in patients with arrhythmic/cardiac events compared to those without events (see FIGS. 16C-16D for QRSd).

In DCM patients, ROC analysis was used to evaluate the performance characteristics of QRSp Mean compared to QRSd. The area under the ROC curve trended to be greater (p>0.05) for QRSp Mean than QRSd. Using a QRSp Mean cutpoint of ≥2.25, the sensitivity and negative predictive value for identifying arrhythmic events were 100% and 100%, respectively (see FIG. 17A). With the same cutpoint, the sensitivity and negative predictive value of QRSp Mean in identifying cardiac events were 90% and 95%, respectively (see FIG. 17B). In comparison, the sensitivity and negative predictive value for QRSd≥120 ms was lower for both arrhythmic and cardiac events, while there was no difference in specificity and positive predictive value (see FIGS. 17A-17B).

TABLE 12

DCM Patient Characteristics

|  | DCM Population (N = 38) | Arrhythmic Event Negative (N = 31) | Arrhythmic Event Positive (N = 7) | P | Cardiac Event Negative (N = 28) | Cardiac Event Positive (N = 10) | P |
|---|---|---|---|---|---|---|---|
| Follow-Up, mos | 19(13-43) | 18(13-48) | 20(14-35) | 0.44 | 18(13-48) | 27(11-42) | 0.67 |
| Age, yrs | 59 ± 13 | 57 ± 13 | 66 ± 9 | 0.10 | 59 ± 12 | 60 ± 16 | 0.80 |
| Male gender, n(%) | 29(76) | 25(81) | 4(57) | 0.32 | 22(79) | 7(70) | 0.67 |
| LVEF, % | 25 ± 7 | 26 ± 7 | 22 ± 8 | 0.25 | 26 ± 8 | 23 ± 7 | 0.33 |
| LVEF < 35%, n(%) | 34(90) | 28(90) | 6(86) | 1.00 | 25(89) | 9(90) | 1.00 |
| NYHA functional class, n(%) | | | | | | | |
| I | 14(37) | 10(32) | 4(57) | 0.65 | 9(32) | 5(50) | 0.17 |
| II | 16(42) | 14(45) | 2(29) | | 14(50) | 2(20) | |
| III | 7(18) | 6(19) | 1(14) | | 5(18) | 2(20) | |
| IV | 1(3) | 1(3) | 0(0) | | 0(0) | 1(10) | |
| Co-morbidities | | | | | | | |
| Hypertension, n(%) | 17(45) | 15(48) | 2(29) | 0.43 | 14(50) | 3(30) | 0.46 |
| Diabetes, n(%) | 17(45) | 12(39) | 5(71) | 0.21 | 11(39) | 6(60) | 0.29 |
| Hyperlipidemia, n(%) | 19(50) | 13(42) | 6(86) | 0.09 | 11(39) | 8(80) | 0.06 |
| Smoking history, n(%) | 21(55) | 16(52) | 5(71) | 0.43 | 15(54) | 6(60) | 1.00 |
| Prior revascularization, n(%) | 2(5) | 2(7) | 0(0) | 1.00 | 2(7) | 0(0) | 1.00 |
| History of atrial fibrillation, n(%) | 12(32) | 10(32) | 2(29) | 1.00 | 10(36) | 2(20) | 0.45 |
| Renal dysfunction*, n(%) | 9(24) | 7(23) | 2(29) | 1.00 | 7(25) | 2(20) | 1.00 |
| Medications | | | | | | | |
| Beta-blocker, n(%) | 38(100) | 31(100) | 7(100) | 1.00 | 28(100) | 10(100) | 1.00 |
| ACE-I/ARB, n(%) | 36(95) | 29(94) | 7(100) | 1.00 | 26(93) | 10(100) | 1.00 |
| Diuretic, n(%) | 33(87) | 27(87) | 6(86) | 1.00 | 24(86) | 9(90) | 1.00 |
| Class III anti-arrhythmic, n(%) | 3(8) | 2(7) | 1(14) | 0.47 | 2(7) | 1(10) | 1.00 |
| Calcium channel blockers, n(%) | 1(3) | 1(3) | 0(0) | 1.00 | 1(4) | 0(0) | 1.00 |

TABLE 12-continued

DCM Patient Characteristics

|  | DCM Population (N = 38) | Arrhythmic Event Negative (N = 31) | Arrhythmic Event Positive (N = 7) | P | Cardiac Event Negative (N = 28) | Cardiac Event Positive (N = 10) | P |
|---|---|---|---|---|---|---|---|
| Lipid-lowering agents, n(%) | 22(58) | 16(52) | 6(86) | 0.20 | 14(50) | 8(80) | 0.14 |
| Antiplatelet agents, n(%) | 14(37) | 10(32) | 4(57) | 0.39 | 10(36) | 4(40) | 1.00 |

*eGFR < 61 mL/min/1.73 m$^2$

TABLE 13

DCM ECG Characteristics

|  | DCM Population (N = 38) | Arrhythmic Event Negative (N = 31) | Arrhythmic Event Positive (N = 7) | P | Cardiac Event Negative (N = 28) | Cardiac Event Positive (N = 10) | P |
|---|---|---|---|---|---|---|---|
| Baseline heart rate, bpm | 72 ± 14 | 72 ± 13 | 75 ± 19 | 0.67 | 72 ± 13 | 75 ± 16 | 0.50 |
| Repolarization Parameters |  |  |  |  |  |  |  |
| QT Interval, ms | 421 ± 50 | 418 ± 49 | 433 ± 58 | 0.49 | 421 ± 50 | 422 ± 51 | 0.94 |
| QTc interval, ms | 453 ± 35 | 453 ± 34 | 452 ± 43 | 0.92 | 453 ± 35 | 453 ± 36 | 0.97 |
| Depolarization parameters |  |  |  |  |  |  |  |
| QRSd, ms | 114(95-128) | 104(94-122) | 128(118-142) | 0.08 | 102(93-122) | 124(106-140) | 0.07 |
| QRSd ≥ 120 ms, n(%) | 17(45) | 12(39) | 5(71) | 0.21 | 11(39) | 6(60) | 0.29 |
| LBBB, n(%) | 10(26) | 7(23) | 3(43) | 0.09 | 7(25) | 3(30) | 1.00 |
| Presence of fQRS, n(%) | 26(68) | 21(68) | 5(71) | 1.00 | 19(68) | 7(70) | 1.00 |
| QRS Score | 3.0(2.0-6.0) | 3.0(1.5-7.0) | 3.0(3.0-3.5) | 0.82 | 2.5(1.5-6.0) | 3.0(3.0-6.0) | 0.40 |
| QRS Fractionation Index | 7.8(5.8-9.0) | 7.6(5.8-8.9) | 8.4(7.0-10.0) | 0.49 | 7.4(5.8-8.8) | 8.8(7.1-9.0) | 0.12 |
| QRSp Mean | 1.8(1.0-3.0) | 1.7(0.8-2.8) | 2.5(2.4-3.0) | 0.027 | 1.6(0.8-2.3) | 2.6(2.3-3.3) | 0.009 |

DISCUSSION

Since QRS slurs are minor perturbations in the QRS waveform, it has been determined by the inventors that conduction delays associated with them are unlikely to be clinically relevant in arrhythmogenesis. Thus by only considering QRS peaks in the QRSp detection and analysis method, the QRS slur components are not unduly weighted.

In accordance with the teachings herein, it was also found that shorter multiple beat QRS averages (e.g. 10-beat) provided greater sensitivity in identifying abnormal QRS peaks than a single longer QRS average (e.g. 100-beat). QRS peaks may be influenced by minor changes in the precordial lead position on the chest wall during respiration. Consequently, longer signal averaged (SA) ECG windows may cause averaging and undervaluing of these peaks. Another consideration in detecting QRS peaks is the use of high resolution ECG recordings with sampling rates over 1000 Hz. By improving detection of QRS peaks, the QRSp methods described herein may distinguish normal subjects from patients with cardiomyopathy and further identify those patients with cardiomyopathy at risk of ventricular arrhythmias.

The QRSp methods described in the retrospective clinical study distinguish normal subjects from patients with cardiomyopathy. Furthermore, it was found in the prospective clinical study that an embodiment of the QRSp methods described herein distinguished cardiomyopathy patients with ventricular arrhythmias from those without ventricular arrhythmias. In particular, the QRSp Mean metric, which is derived from the QRS peak scores in all precordial leads, independently predicted ventricular arrhythmias and cardiac events in patients with cardiomyopathy and no prior history of ventricular arrhythmias. A QRSp Mean value≥2.25 had a sensitivity and negative predictive value of 100% and 100% for arrhythmic events, respectively in this population; thereby identifying all patients at risk of ventricular arrhythmias.

The QRSp methods described in the prospective clinical study outperformed traditional QRS morphologic metrics, such as QRSd, fQRS, QRS score, and QRS FI. In particular, QRSp Mean was more accurate in identifying patients with ventricular arrhythmias and cardiac events than QRSd, which is commonly used to risk stratify cardiomyopathy patients [12]. The signal averaged ECG-based methods that have been used to evaluate QRS morphology have produced sensitivities no better than 69% in identifying patients with ventricular arrhythmias [3-5]. Thus, the QRSp methods described herein have the potential to improve ventricular arrhythmia risk assessment in patients with heart disease. Accurate risk stratification may guide patient selection for cardiac therapy, in particular prophylactic defibrillator therapy.

One challenge may be the potential for noise to produce false QRSp detections, which may be due to using a smaller set of beats for averaging. However, a correlation between QRSp and RMS −ST noise levels was not found in both the retrospective and prospective clinical studies. Moreover, the simulations suggest that the likelihood of a false positive may be reduced if beats with RMS-ST values>9.7 pV are excluded from analysis.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments described herein, the general scope of which is defined in the appended claims.

REFERENCES

[1] N. C. Flowers, L. G. Horan, J. R. Thomas, and W. J. Tolleson, "The anatomic basis for high-frequency components in the electrocardiogram," *Circulation*, vol. 39, no. 4, pp. 531-539, 1969.

[2] H. E. I. K. Riekkinen and P. E. N. T. Rautahaiju, "Body position, electrode level, and respiration effects on the Frank lead electrocardiogram," *Circulation*, vol. 53, no. 1, pp. 40-45, 1976.

[3] P. Lander, P. Gomis, R. Goyal, E. J. Berbari, P. Caminal, R. Lazzara, and J. S. Steinberg, "Analysis of abnormal intra-QRS potentials Improved predictive value for arrhythmic events with the signal-averaged electrocardiogram," *Circulation*, vol. 95, no. 6, pp. 13861393, 1997.

[4] C. C. Lin, "Enhancement of accuracy and reproducibility of parametric modeling for estimating abnormal intra-QRS potentials in signal-averaged electrocardiograms," *Medical engineering & physics*, vol. 30, no. 7, pp. 834-842, 2008.

[5] P. Korhonen, T. Husa, T. Konttila, I. Tierala, M. Makijarvi, H. Vaananen, J. Ojanen, A. Vehtari, and L. Toivonen, "Fragmented QRS in prediction of cardiac deaths and heart failure hospitalizations after myocardial infarction," *Annals of Noninvasive Electrocardiology*, vol. 15, no. 2, pp. 130-137, 2010.

[6] J. Pan and W. J. Tompkins, "A real-time QRS detection algorithm," *Biomedical Engineering, IEEE Transactions on*, no. 3, pp. 230-236, 1985.

[7] S. E. Bobbs, N. M. Schmitt, and H. S. Ozemek, "QRS detection by template matching using real-time correlation on a microcomputer," *Journal of clinical engineering*, vol. 9, no. 3, pp. 197-212, 1984.

[8] C. R. Meyer and H. N. Keiser, "Electrocardiogram baseline noise estimation and removal using cubic splines and state-space computation techniques," *Computers and Biomedical Research*, vol. 10, no. 5, pp. 459-470, 1977.

[9] Breslow, N. E., "Analysis of Survival Data under the Proportional Hazards Model", International Statistical Review/Revue Internationale de Statistique, 43(1): pp. 45-57, 1975.

[10] Suszko A, Dalvi, R, Das M, Chauhan V S. "Quantifying abnormal QRS peaks using a novel time-domain peak detection algorithm. Application in patients with cardiomyopathy at risk of sudden death.", IEEE International Conf. Electro/Information Technology, May 2015; pp. 20-24.

[11] G. Breithardt, M. E. Cain, N. El-Sherif, N. C. Flowers, V. Hombach, M. Janse, M. B. Simson, and G. Steinbeck, "Standards for analysis of ventricular late potentials using high-resolution or signal-averaged electrocardiography: a statement by a task force committee of the European Society of Cardiology, the American Heart Association, and the American College of Cardiology," *Journal of the American College of Cardiology*, vol. 17, no. 5, pp. 999-1006, 1991.

[12] Lee D S, Hardy J, Yee R, Healey J S, Birnie D, Simpson C S, Crystal E, Mangat I, Nanthakumar K, Wang X, Krahn A D, Dorian P, Austin P C, Tu J V; "Investigators of the Ontario ICD Database. Clinical Risk Stratification for Primary Prevention Implantable Cardioverter Defibrillators.", Circ. Heart Fail. 2015 September; 8(5): pp. 927-37.

[13] Das M K, Saha C, El Masry H, et al., "Fragmented QRS on a 12-lead ECG: A predictor of mortality and cardiac events in patients with coronary artery disease.", Heart Rhythm 2007; 4: pp. 1385-1392.

[14] Korhonen P, Husa T, Konttila T, Tierala I, Makijarvi M, Vaandnen H, Ojanen J, Vehtari A, Toivonen L., "Fragmented QRS in prediction of cardiac deaths and heart failure hospitalizations after myocardial infarction.", Ann Noninvasive Electrocardiol. 2010 April; 15(2): pp. 130-7.

The invention claimed is:

1. A method of assessing a risk of ventricular arrhythmias for a patient, the method comprising:
receiving ECG data obtained from the patient via an input interface;
analyzing the received ECG data to detect abnormal QRS peaks using a QRS peak analysis module that is executed by a processing unit that is coupled to the input interface, the analysis of the received ECG data for a given ECG lead including:
preprocessing the received ECG data,
generating a preprocessed global version from a first number of QRS complexes from a section of the preprocessed received ECG data, wherein the preprocessed global version is generated from Y beats of the section of preprocessed received ECG data, and
generating a preprocessed local version from a second number of QRS complexes from the section of the preprocessed received ECG data, where the second number is smaller than the first number, wherein the preprocessed local version is generated from X beats of the section of preprocessed received ECG data, where X and Y are real numbers and the X beats of ECG data are contained in the Y beats of ECG data;
identifying peaks found to be present in only the preprocessed local version by comparing the preprocessed local version and the preprocessed global version;
defining the peaks found to be present in only the preprocessed local version as being abnormal QRS peaks;
determining the risk of ventricular arrhythmias for the patient based on the detected abnormal QRS peaks using a ventricular arrhythmia assessment module that is executed by the processing unit; and
providing an indication of the risk of ventricular arrhythmias for the patient via an output interface that is coupled to the processing unit.

2. The method of claim 1, wherein the method comprises acquiring the ECG data from the patient using one or more ECG recording leads or obtaining the ECG data from a data store in which the ECG data having already been preprocessed.

3. The method of claim 2, wherein preprocessing the received ECG data comprises applying a QRS template and optionally applying filtering.

4. The method of claim 2, wherein the received ECG data is high resolution data that is obtained using a sampling rate of at least 1,000 Hz.

5. The method of claim 1, wherein the act of analyzing the received ECG data from a given ECG recording lead comprises:

generating the preprocessed local version by generating a local QRS (lQRS) signal by applying averaging to the X beats of the section of preprocessed received ECG data;

generating the preprocessed global version by generating a global QRS (gQRS) signal by applying filtering and averaging to the Y beats of the section of preprocessed received ECG data; and comparing the preprocessed local version and the preprocessed global version comprises comparing the lQRS signal with the gQRS signal.

6. The method of claim 5, wherein the gQRS signal is generated by filtering the Y beats of preprocessed ECG data using a smoothing filter and then applying averaging to the filtered Y beats of ECG data, where the X beats of ECG data is a short data window and the Y beats of ECG data is a larger data window that is at least one order of magnitude larger than the short data window.

7. The method of claim 5, wherein the comparing comprises:

identifying positive and negative peaks in the lQRS and gQRS signals;

determining abnormal positive peaks in the lQRS signal by counting the number of positive peaks in the lQRS signal within ±M msec of each positive peak in the gQRS signal while excluding the nearest or greatest amplitude lQRS peak within ±M msec of each positive peak in the gQRS signal;

determining abnormal negative peaks in the lQRS signal by counting the number of negative peaks in the lQRS signal within ±M msec of each negative peak in the gQRS signal while excluding the nearest or least amplitude lQRS peak within ±M msec of each negative peak in the gQRS signal; and determining a QRS peak (QRSp) score based on the total determined abnormal positive peaks and the abnormal negative peaks in the lQRS signal.

8. The method of claim 7, wherein the QRSp score for the given ECG recording lead is an average, median or maximum of the set of QRSp scores derived from the given ECG recording lead and the QRSp score for the patient is an average, median or maximum of the QRSp scores for ECG data obtained from at least a portion of the ECG recording leads.

9. The method of claim 7, wherein the act of determining the risk of ventricular arrhythmia for the patient comprises selecting a quantitative risk measure associated with the QRSp score for the patient based on a multivariable regression model that is generated based on QRSp scores determined for healthy subject, patients with heart disease but no ventricular arrhythmias and patients with heart disease in whom ventricular arrhythmias have occurred.

10. The method of claim 5, wherein the method further comprises determining the lQRS signal using a sliding average of X beats of ECG data within the Y beats of ECG data and determining a set of QRSp scores for each set of averaged X beats of ECG data.

11. The method of claim 1, wherein the ECG data comprises several sets of ECG data obtained using different ECG leads and the QRSp score is determined for each set of ECG data.

12. A system for assessing risk of ventricular arrhythmias for a patient, wherein the system comprises:

an input interface for receiving ECG data obtained from the patient;

an output interface for providing an indication of the risk of ventricular arrhythmia for the patient; and a processing unit coupled to the input and the output interfaces, the processing unit being configured to analyze the received ECG data using a QRS peak analysis module to detect abnormal QRS peaks; determine the risk of ventricular arrhythmia for the patient based on detected abnormal QRS peaks using a ventricular arrhythmia assessment module; provide the indication of the risk of ventricular arrhythmia for the patient using the output interface, where the analysis of the received ECG data for a given ECG lead includes preprocessing the received ECG data, generating a preprocessed global version from a first number of QRS complexes from a section of the preprocessed received ECG data, wherein the preprocessed global version is generated from Y beats of the section of preprocessed received ECG data, and generating a preprocessed local version from a second number of QRS complexes from the section of the preprocessed received ECG data, where the second number is smaller than the first number, wherein the preprocessed local version is generated from X beats of the section of preprocessed received ECG data, where X and Y are real numbers and the X beats of ECG data are contained in the Y beats of ECG data; identifying peaks found to be present in only the preprocessed local version by comparing the preprocessed local version and the preprocessed global version; and defining the peaks found to be present in only the preprocessed local version as being the abnormal QRS peaks.

13. The system of claim 12, wherein the system further comprises:

a sensor unit comprising sensors for sensing ECG data from the patient during use; and a data acquisition unit coupled to the sensor unit and the processing unit for acquiring the sensed ECG data.

14. The system of claim 12, wherein the processing unit is configured to analyze the ECG data from a given ECG recording lead by:

generating the preprocessed local version by generating a local QRS (lQRS) signal by applying averaging to the X beats of the section of preprocessed received ECG data;

generating the preprocessed global version by generating a global QRS (gQRS) signal by applying filtering and averaging to the Y beats of the section of preprocessed received ECG data; and to compare the preprocessed local version and the preprocessed global version by comparing the lQRS signal with the gQRS signal for defining peaks found to be present in only the preprocessed local version as being the abnormal QRS peaks.

15. The system of claim 14, wherein the gQRS signal is generated by filtering the Y beats of preprocessed ECG data using a smoothing filter and then applying averaging to the filtered Y beats of ECG data, where the X beats of ECG data is a short data window and the Y beats of ECG data is a larger data window that is at least one order of magnitude larger than the short data window.

16. The system of claim 14, wherein the processor is further configured to determine the lQRS signal using a sliding average of the X beats of ECG data within the Y beats of ECG data and determining a set of QRSp scores for each set of averaged X beats of ECG data.

17. The system of claim 14, wherein the processor is configured to perform the comparing by:

identifying positive and negative peaks in the lQRS and gQRS signals;

determining abnormal positive peaks in the IQRS signal by counting the number of positive peaks in the IQRS signal within ±M msec of each positive peak in the gQRS signal while excluding the nearest or greatest amplitude IQRS peak within ±M msec of each positive peak in the gQRS signal;

determining abnormal negative peaks in the IQRS signal by counting the number of negative peaks in the IQRS signal within ±M msec of each negative peak in the qQRS signal while excluding the nearest or least amplitude IQRS peak within ±M msec of each negative peak in the gQRS signal; and determining a QRS peak (QRSp) score based on the total determined abnormal positive peaks and the abnormal negative peaks in the IQRS signal.

18. The system of claim 17, wherein the QRSp score for the given ECG recording lead is an average, median or maximum of the set of QRSp scores derived from the given ECG recording lead and the QRSp score for the patient is an average, median or maximum of the QRSp scores for ECG data obtained from at least a portion of the ECG recording leads.

19. The system of claim 17, wherein the act of determining the risk of ventricular arrhythmia for the patient comprises selecting a quantitative risk measure associated with the QRSp score for the patient based on a multivariable regression model that is generated based on QRSp scores determined for healthy subjects, patients with heart disease but no ventricular arrhythmias and patients with heart disease in whom ventricular arrhythmias have occurred.

20. A non-transitory computer readable medium comprising a plurality of instructions that are executable on a processing unit of a device for adapting the device to implement a method for assessing risk of ventricular arrhythmias for a patient, wherein the method comprises:

receiving ECG data obtained from the patient from an input interface that is coupled to the processing unit;

analyzing the received ECG data to detect abnormal QRS peaks using a QRS peak analysis module that is executed by the processing unit, the analysis of the received ECG data for a given ECG lead including preprocessing the received ECG data, generating a preprocessed global version from a first number of QRS complexes from a section of the preprocessed received ECG data, wherein the preprocessed global version is generated from Y beats of the section of preprocessed received ECG data, and generating a preprocessed local version from a second number of QRS complexes from the section of the preprocessed received ECG data, where the second number is smaller than the first number, wherein the preprocessed local version is generated from X beats of the section of preprocessed received ECG data, where X and Y are real numbers and the X beats of ECG data are contained in the Y beats of ECG data;

identifying peaks found to be present in only the preprocessed local version by comparing the preprocessed local version and the preprocessed global version;

defining the peaks found to be present in only the preprocessed local version as being abnormal QRS peaks;

determining the risk of ventricular arrhythmias for the patient based on the detected abnormal QRS peaks using a ventricular arrhythmia assessment module that is executed by the processing unit; and providing an indication of the risk of ventricular arrhythmias for the patient via an output interface that is coupled to the processing unit.

* * * * *